United States Patent [19]

Khannal et al.

[11] Patent Number: 5,302,601

[45] Date of Patent: * Apr. 12, 1994

[54] 5-SUBSTITUTED IMIDAZO[4,5-C]PYRIDINES

[75] Inventors: Ish K. Khannal, Vernon Hills; Roger Nosal, Buffalo Grove; Richard M. Weier, Lake Bluff; Kirk T. Lentz, Niles, all of Ill.

[73] Assignee: G. D. Searle & Co., Chicago, Ill.

[*] Notice: The portion of the term of this patent subsequent to Apr. 3, 2007 has been disclaimed.

[21] Appl. No.: 973,127

[22] Filed: Nov. 6, 1992

Related U.S. Application Data

[63] Continuation-in-part of Ser. No. 670,133, Mar. 15, 1991, Pat. No. 5,227,384, which is a continuation-in-part of Ser. No. 317,871, Mar. 6, 1989, Pat. No. 5,019,581, which is a continuation-in-part of Ser. No. 167,671, Mar. 14, 1988, Pat. No. 4,914,108.

[51] Int. Cl.$^5$ .................. A61K 31/395; C07D 471/04
[52] U.S. Cl. ..................................... 514/303; 546/118
[58] Field of Search ........................ 514/303; 546/118

[56] References Cited

U.S. PATENT DOCUMENTS

| | | | |
|---|---|---|---|
| 4,327,100 | 4/1982 | Austel et al. | 424/256 |
| 4,336,257 | 6/1982 | Baldwin | 424/256 |
| 4,914,108 | 4/1990 | Khanna et al. | 514/303 |
| 5,019,581 | 5/1991 | Khanna et al. | 514/303 |

FOREIGN PATENT DOCUMENTS

0260613A2  3/1988  European Pat. Off. .

*Primary Examiner*—C. Warren Ivy
*Assistant Examiner*—James H. Turnipseed
*Attorney, Agent, or Firm*—Joy Ann Serauskas; Roger A. Williams

[57] ABSTRACT

The present invention relates to a class of compounds represented by the formula

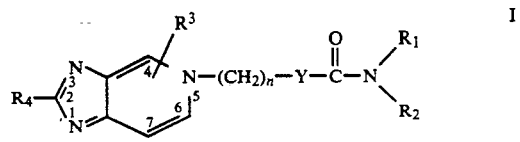

or a pharmaceutically acceptable salt thereof useful in the treatment of diseases or disorders mediated by platelet activating factor (PAF).

10 Claims, No Drawings

5-SUBSTITUTED IMIDAZO[4,5-C]PYRIDINES

This application is a continuation-in-part of U.S. Ser. No. 07/670,133, filed Mar. 15, 1991, now U.S. Pat. No. 5,227,385, which is a continuation-in-part of U.S. Ser. No. 07/317,871, filed Mar. 6, 1989, now U.S. Pat. No. 5,019,581, which is a continuation-in-part of U.S. Ser. No. 07/167,671, filed Mar. 14, 1988, now U.S. Pat. No. 4,914,108.

FIELD OF THE INVENTION

This invention is in the field of mammalian therapeutics and relates to compounds for treatment of mammalian diseases such as inflammation, cardiovascular disorders, asthma and other diseases. Of particular interest is a class of 5-substituted imidazo [4,5-c] pyridines useful for treatment of cardiovascular and immuno-inflammatory related disorders mediated by platelet activating factor (PAF).

BACKGROUND OF THE INVENTION

Platelet activating factor (PAF) has been associated with various biological activities and pathways, thus making it an important mediator responsible for a variety of physiological processes including, but not limited to, activation and aggregation of platelets, smooth muscle contraction, pathogenesis of immune complex deposition, inflammation, immunomodulation, respiratory, cardiovascular and intravascular alterations. These physiological processes are associated with a large group of diseases, such as, for example, cardiovascular disorders, asthma, lung edema, endotoxin shock, adult respiratory distress syndrome and inflammatory diseases, autoimmunization and graft rejection.

U.S. Pat. No. 4,804,658 discloses a class of imidazopyridine derivatives useful in the treatment of diseases or disorders mediated by platelet activating factor. The present invention is distinct from this disclosure in that in the present invention the benzamide moiety is attached to the nitrogen (position 5) which makes up the six membered ring of the imidazopyridine ring system as opposed to the disclosure wherein the benzamide moiety is attached to one of the nitrogens which makes up the five membered ring of the imidazopyridine ring system.

SUMMARY OF THE INVENTION

The present invention relates to a novel class of compounds represented by the formula:

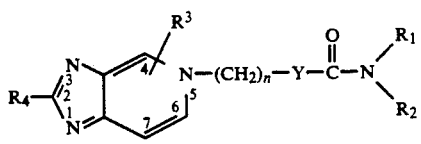

I or a pharmaceutically acceptable acid addition salt thereof, wherein $R_1$ and $R_2$ are each independently selected from hydrogen; straight or branched chain alkyl of 1 to 15 carbon atoms; cycloalkyl having 3 to 8 carbon atoms; substituted cycloalkyl which can be substituted one or more by alkyl of 1 to 6 carbon atoms; bicycloalkyl having 3 to 8 carbon atoms in each ring; heterocyclicalkyl having 4 to 8 carbon atoms which can be optionally substituted by alkyl of 1 to 6 carbon atoms; heteroaromatic having 5 or 6 carbon atoms which can be optionally substituted by alkyl having 1 to 6 carbon atoms; phenyl; substituted phenyl which can be substituted one or more by a group independently selected from alkyl having 1 to 6 carbon atoms or halogen; straight or branched alkenyl having 3 to 15 carbon atoms with the proviso that the double bond of the alkenyl group cannot be adjacent to the nitrogen; cycloalkenyl having 5 to 8 carbon atoms with the proviso that the double bond cannot be adjacent to the nitrogen; and $R_1$ and $R_2$ cannot both be hydrogen;

Y is phenyl or phenyl substituted once or more than at one or more of the 2, 3, 5 or 6 positions of the phenyl ring by substituents independently selected from the group consisting of alkoxy having 1 to 6 carbon atoms; halogen wherein the halogen is selected from bromo, fluoro, or chloro; straight or branched chain alkyl having 1 to 6 carbon atoms; substituted straight or branched chain alkyl which can be substituted one or more by halogen; thioalkyl wherein the alkyl has 1 to 6 carbon atoms; alkoxyalkyl wherein the alkyl groups are each 1 to 6 carbon atoms; hydroxyalkyl wherein the alkyl has 1 to 6 carbon atoms; alkylthioalkyl wherein the alkyl groups are each 1 to 6 carbon atoms; cyano; mercaptoalkyl wherein the alkyl has 1 to 6 carbon atoms; hydroxy; amino; alkylamino wherein the alkyl group has 1 to 6 carbon atoms; and dialkylamino wherein the alkyl groups are each 1 to 6 carbon atoms;

n is an integer of 1 to 5;

$R_3$ is a group substituted at one or more of the 4, 6, or 7 positions of the pyridine ring said group being independently selected from hydrogen; alkyl having 1 to carbon atoms; halogen wherein the halogen is selected from bromo, fluoro or chloro; and alkoxy having 1 to 6 carbon atoms; and $R_4$ is hydrogen or alkyl having 1 to 6 carbon atoms;

The invention further relates to pharmaceutical compositions comprising a compound of formula I. Such compounds and compositions have potent and specific PAF antagonistic activities and are thereby useful in the treatment of various diseases or disorders mediated by PAF, for example inflammation, cardiovascular disorders, asthma, lung edema, and adult respiratory distress syndrome.

A preferred embodiment of the present invention are compounds of the formula:

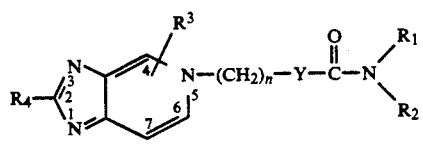

I or a pharmaceutically acceptable acid addition salt thereof, wherein $R_1$ and $R_2$ are each independently selected from hydrogen; straight or branched chain alkyl having 1 to 15 carbon atoms; cycloalkyl having 3 to 8 carbon atoms; substituted cycloalkyl which can be substituted one or more by alkyl of 1 to 6 carbon atoms; bicycloalkyl having 3 to 8 carbon atoms in each ring; phenyl; substituted phenyl which can be substituted one or more by a group independently selected from alkyl having 1 to 6 carbon atoms and halogen; straight or branched alkenyl having 3 to 15 carbon atoms with the proviso that the double bond of the alkenyl group cannot be adjacent to the nitrogen; cycloalkenyl having 5 to 8 carbon atoms with the proviso that the double bond cannot be adjacent to the nitrogen; and $R_1$ and $R_2$ cannot both be hydrogen;

Y is phenyl or phenyl substituted once or more than at one or more of the 2, 3, 5 or 6 positions of the phenyl ring by substituents independently selected from the group consisting of alkoxy having 1 to 6 carbon atoms; halogen wherein the halogen is selected from bromo, fluoro, or chloro; straight or branched chain alkyl having 1 to 6 carbon atoms; substituted straight or branched chain alkyl which can be substituted one or more by halogen;

n is an integer of 1 to 5;

$R_3$ is a group substituted at one or more of the 4, 6, or 7 positions of the pyridine ring said group being independently selected from hydrogen; alkyl having 1 to 6 carbon atoms; halogen wherein the halogen is selected from bromo, fluoro or chloro; and alkoxy having 1 to 6 carbon atoms; and $R_4$ is hydrogen or alkyl of 1 to 6 carbon atoms.

A further embodiment of the present invention are compounds of the formula:

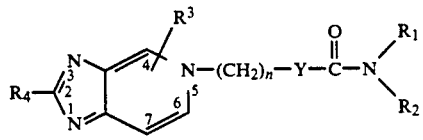

I or a pharmaceutically acceptable acid addition salt thereof, wherein $R_1$ and $R_2$ are each independently selected from hydrogen; straight or branched chain alkyl having 1 to 15 carbon atoms; cycloalkyl having 3 to 8 carbon atoms; substituted cycloalkyl which can be substituted one or more by alkyl having 1 to 6 carbon atoms; phenyl; substituted phenyl which can be substituted one or more by the group independently selected from alkyl having 1 to 6 carbon atoms and halogen; and $R_1$ and $R_2$ cannot both be hydrogen;

Y is phenyl or phenyl substituted once or more than at one or more of the 2, 3, 5 or 6 position of the phenyl ring by substituents independently selected from the group consisting of alkoxy having 1 to 6 carbon atoms; halogen wherein the halogen is selected from bromo, fluoro, or chloro; and straight or branched chain alkyl having 1 to 6 carbon atoms;

n is an integer of 1 to 5;

$R_3$ is a group substituted at one or more of the 4, 6, or 7 positions of the pyridine ring said group being independently selected from hydrogen and alkyl having 1 to 6 carbon atoms;

$R_4$ is hydrogen or alkyl having 1 to 6 carbon atoms.

As used herein the term "alkyl having 1 to 15 carbon atoms": refers to straight chain or branched chain hydrocarbon groups having from one to fifteen carbon atoms. Illustrative of such alkyl groups are methyl, ethyl, propyl isopropyl, butyl, isobutyl, pentyl, neopentyl, hexyl, isohexyl, octyl, decyl and the like.

As used herein the term "cycloalkyl having 3 to 8 carbon atoms" includes cycloalkyl groups having from three to eight carbons. Illustrative of such cycloalkyl groups are cyclopropyl, cyclobutyl, cyclopentyl, cyclohexyl, cycloheptyl, cyclooctyl and the like.

As used herein the term halogen includes fluoro, chloro and bromo.

As used herein the term "alkenyl having 2 to 15 carbon atoms" refers to straight or branched unsaturated hydrocarbon groups having from 2 to 15 carbon atoms. Illustrative of such alkenyl groups are 2-propenyl, hexenyl, octenyl, decenyl and the like.

As used herein the term "alkoxy wherein the alkyl is 1 to 6 carbon atoms" refers to straight or branched chain ethers. Illustrative of such groups are methoxy, ethoxy, propoxy, butoxy, isopropoxy and the like.

The term "hydroxyalkyl" refers to straight or branched alkyl group having one to six atoms wherein the group may be substituted with one or more hydroxyl groups.

The term "thioalkyl" refers to straight or branched thio-containing radicals, respectively having alkyl portions of one to six attached.

The term "mercaptoalkyl" refers to a terminal mercapto group attached to an alkyl portion of one to six carbon atoms which can be straight or branched.

The term "heterocyclicalkyl" refers to a cyclic radicals having 5 to 8 carbon atoms wherein one or more of the carbons is replaced by nitrogen, sulfur or oxygen.

The term heteroaromatic refers to cyclic radicals having 5 or 6 ring carbon atoms which can be optionally substituted one or more times by alkyl of 1 to 6 carbon atoms with the understanding that the 5 membered carbon atom ring is replaced one or more times by nitrogen, sulfur or oxygen and when more than one hetero atom exists in the 5-membered ring one hetero atom must be nitrogen; the six membered carbon atom ring is replaced one or more times by nitrogen.

Included within the embodiments of the present invention are the tautomeric forms of the described compounds, isomeric forms including geometric isomers, enantiomers and diastereoisomers, and the pharmaceutically acceptable salts thereof.

The term "pharmaceutically acceptable acid addition salt" refers to a salt prepared by contacting a compound of formula (I) with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

The compounds of formula (I) may be prepared in accordance with the following procedures.

Imidazopyridine which is represented by the following formula

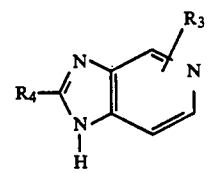

II wherein $R_3$ and $R_4$ are defined as before is reacted with a haloalkyl, alkylsulfonyloxy or arylsulfonyloxyalkylbenzamide which is represented by the following formula

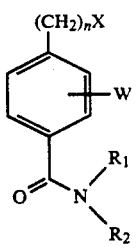

III wherein $R_1$ and $R_2$ and n are defined as before and X is chloro, bromo, methanesulfonyloxy or p-toulenesulfonyloxy to give the compounds of formula I. It is understood that the haloalkylbenzamide can also be substituted by halogen, alkyl of 1 to 6 carbon atoms; alkoxy wherein the alkyl is 1 to 6 carbon atoms: thioalkyl wherein the alkyl is 1 to 6 carbon atoms; alkoxy alkyl wherein the alkyl is 1 to 6 carbon atoms; hydroxyalkyl wherein the alkyl is 1 to 6 carbon atoms; alkylthioalkyl wherein the alkyl is 1 to 6 carbon atoms; cyano; mercaptoalkyl wherein the alkyl is 1 to 6 carbon atoms; hydroxy; amino; alkylamino wherein the alkyl group are each 1 to 6 carbon atoms and dialkylamino wherein the alkyl group are each 1 to 6 carbon atoms. These groups are represented by the letter W in formula III.

Preferred reaction conditions for the above-identified procedure include heating overnight at room temperature to 90° C. a solution of haloalkylbenzamide and imidazopyridine in a solvent such as dimethylacetamide, dimethylformamide, or acetonitrile (approximately 0.1M in each). After heating overnight the reaction solvent is removed in vacuo and the residue diluted with water and basified with ammonium hydroxide. The aqueous solution is extracted with chloroform and the combined organic extracts are backwashed with saturated aqueous sodium chloride solution. The organic solution is dried over sodium sulfate or magnesium sulfate, the drying agent filtered and the filtrate concentrated in vacuo to give the crude product. Purification is effected by chromatography on silica gel using mixtures of chloroform, ethanol and ammonium hydroxide.

A preferred work up for the above-described procedure is to cool the reaction solution which had been heated overnight to room temperature and remove the solvent under reduced pressure at <45° C. The residue obtained is triturated with excess of dry ether and filtered. The crude product is purified by chromatography.

SYNTHESIS OF INTERMEDIATES

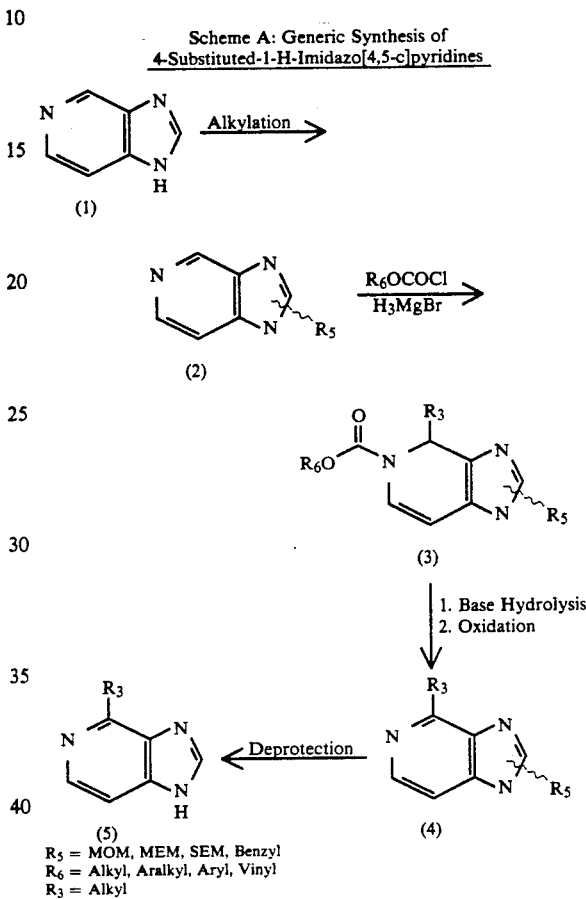

Scheme A: Generic Synthesis of 4-Substituted-1-H-Imidazo[4,5-c]pyridines $R_5$ = MOM, MEM, SEM, Benzyl
$R_6$ = Alkyl, Aralkyl, Aryl, Vinyl
$R_3$ = Alkyl

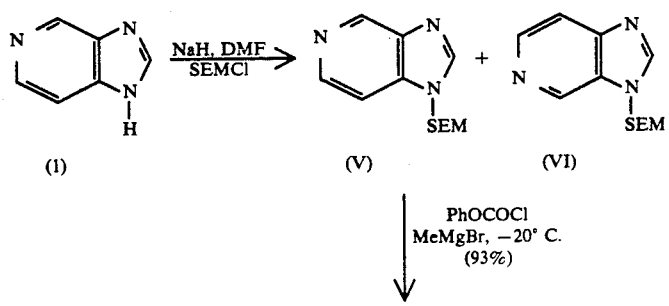

Scheme B: Synthesis of 4-Methyl-1-H-Imidazo[4,5-c]pyridine

-continued

Scheme B: Synthesis of 4-Methyl-1-H-Imidazo[4,5-c]pyridine

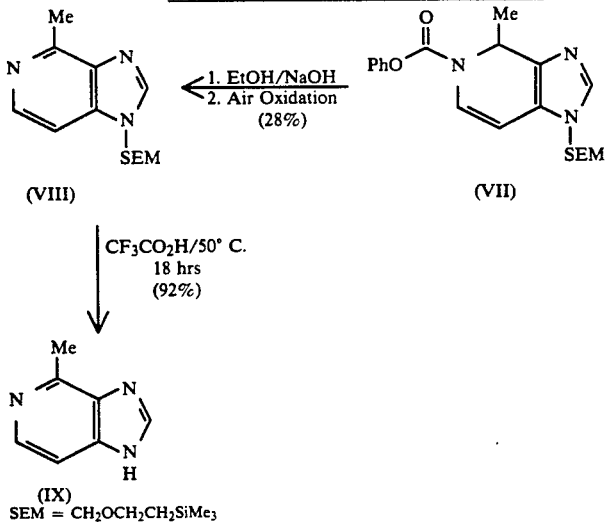

SEM = CH₂OCH₂CH₂SiMe₃

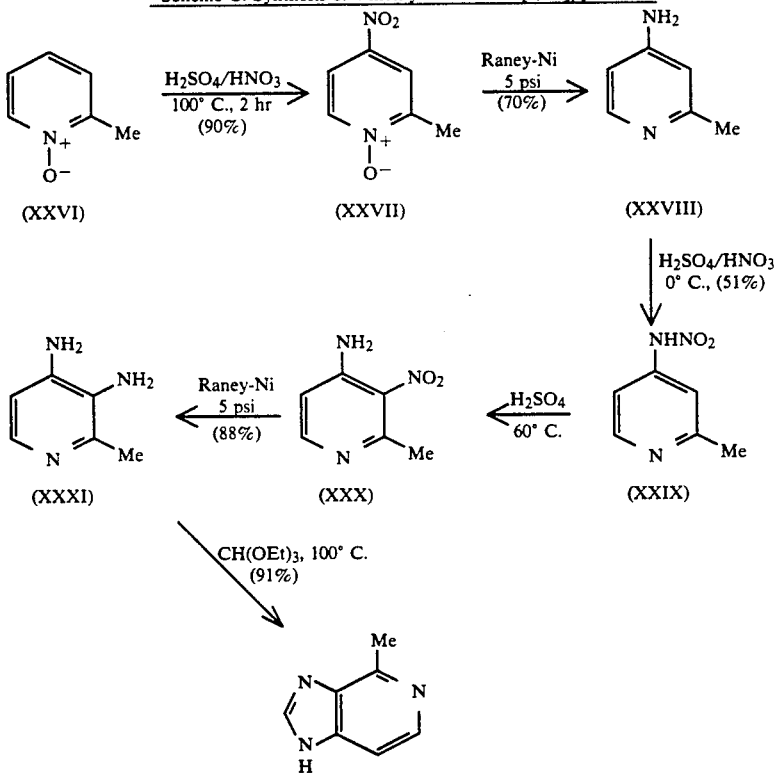

Synthesis of 4-alkyl-imidazo[4,5-c]pyridines

The imidazo[4,5-c]pyridines of structural formula II wherein R₃ is 4-alkyl can be prepared by following the reaction Scheme A. The known imidazopyridine (1) is protected at N-1 or N-3 by reaction with alkyl halides such as 2-(trialkylsilyl)ethoxymethyl chloride, 2-methoxyethoxymethyl chloride, 2-methoxymethyl chloride, or benzyl bromide in the presence of a base such as triethylamine, pyridine, potassium carbonate, cesium carbonate, sodium carbonate, sodium hydride or potassium hydride using a polar aprotic solvent such as dimethylformamide or dimethylacetamide. This reaction is carried out between 0° C. to 50° C. The protected imidazopyridine (2) is activated by an alkyl/aryl or vinyl chloroformate and reacted with arylmagnesium halides. These reactions can be carried out between −30° C. and 20° C. The suitable chloroformate reagents for this reaction are, e.g., methyl chloroformate, ethyl chloroformate, vinyl chloroformate, phenyl chloroformate, trichloroethyl chloroformate, trimethylsilylethoxy chloroformate. The 4-alkylated product (3) bearing a carbamate group at position 5 is treated with aqueous base such as alcoholic (e.g. ethanolic, methanolic, isopropanolic) sodium or potassium hydroxide at from 40° C. to reflux for several hours. The resulting product is oxidized either by bubbling air or using reagents such as chloranil or DDQ to give the aromatized compound 4. The protected group at nitrogen is then removed by judicious choice of conditions to give the targeted 4-alkyl-imidazopyridine 5. For example, SEM, MEM or MOM ether may be removed by treatment with suitable acid such as trifluoroacetic acid or 6N HCl. The benzyl group can be removed by, e.g., catalytic hydrogenation using, for example, palladium on carbon as a catalyst.

hydrogenation with, e.g., Raney-Nickel as the catalyst to give 4-amino derivative (XXVIII). The nitro compound was converted to the 4-nitramine (XXIX) using sulfuric acid/nitric acid and then rearranged using sulfuric acid to 3-nitro-4-amino derivative (XXX). The reduction of the 3-nitro group was carried out as described above and the resulting 3,4-diamino compound (XXXI) cyclized with e.g., triethylorthoformate and catalytic amount of p-toluenesulfonic acid to give the desired 4-methyl-imidazopyridine (IX).

The preparation of unsubstituted imidazo[4,5-c]pyridine (1) is described in U.S. Pat. No. 4,804,658.

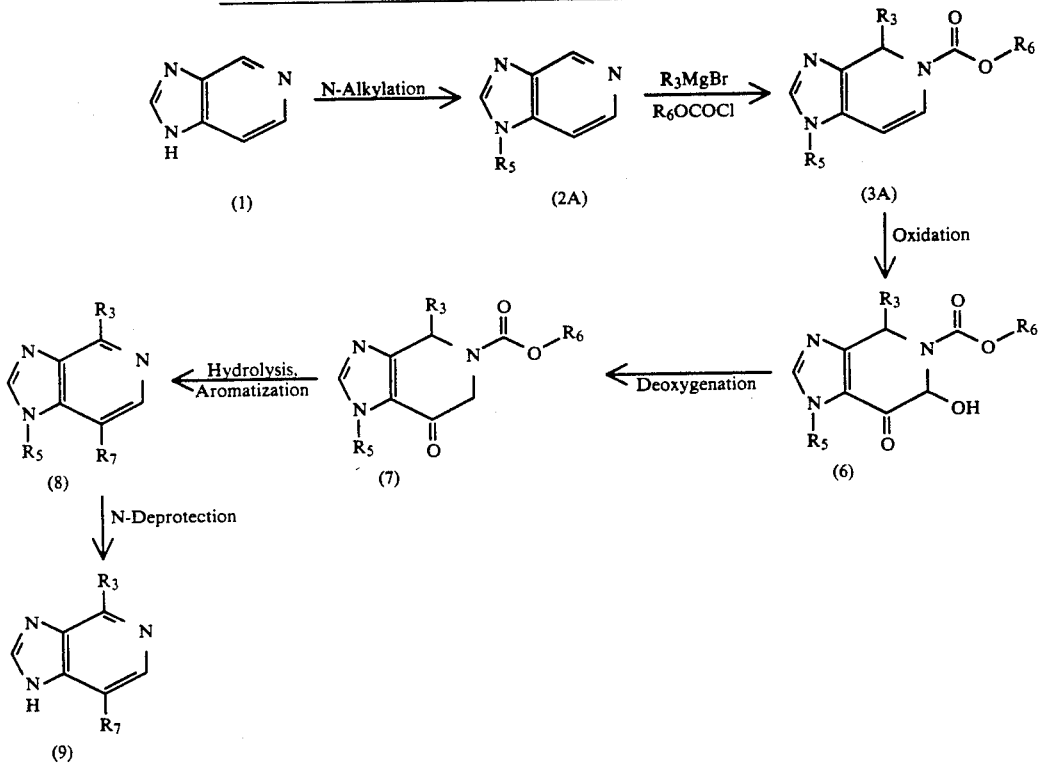

Synthesis of 4-methyl-imidazo[4,5-c]pyridine

The synthesis of 4-methyl-imidazo[4,5-c]pyridine (formula II, $R_3$=4-Me) was carried out by following the reaction Scheme B. Thus, imidazopyridine (1) was protected at the imidazole nitrogen by treating with trimethylsilylethoxymethyl chloride using sodium hydride in dimethylformamide to give V and VI. The intermediate V was reacted with phenyl chloroformate and methylmagnesium bromide and the resulting addition product VII hydrolyzed using aqueous NaOH and oxidized with air to yield VIII. The trimethylsilylethoxymethyl group in VIII was removed by heating with trifluoroacetic acid at 50° C. to give the desired compound IX.

Alternately, 4-methyl-imidazo[4,5-c]pyridine (formula II, $R_3$ =4-Me) can also be synthesized as shown in Scheme C. 2-Picoline-N-oxide (XXVI) was nitrated using a nitrating reagent such as nitric acid/sulfuric acid to give 4-nitro derivative (XXVII) and reduced by Synthesis of 4,7-disubstituted-imidazo[4,5-c]pyridine The synthesis of 4,7-disubstituted imidazo[4,5-c]pyridine can be accomplished as shown in Scheme D. The imidazo[4,5-c]pyridine (1) is protected at N-1 and alkylated at C-4 to give the intermediates 2A and 3A respectively as discussed in Scheme A. The 4-substituted product 3A is treated with an oxidizing agent, e.g., osmium tetroxide, to give the intermediate 6. Removal of the hydroxyl at C-6 can be carried out using reagents such as samarium iodide or chromous ($Cr^{+2}$) salts to give the 7-keto derivative 7. Removal of the carbamate group followed by aromatization can be carried out using conditions elaborated in Scheme A to give the intermediate s. Deprotection of group at N-1 can similarly be achieved as indicated above in Scheme A to give 4,7-disubstituted imidazo[4,5-c]pyridine (9).

The synthesis of 4-methyl-7-methoxy imidazo[4,5-c]pyridine XVI is shown in Scheme E.

Scheme E: Synthesis of 4-methyl-7-methoxy imidazo[4,5-c]pyridine
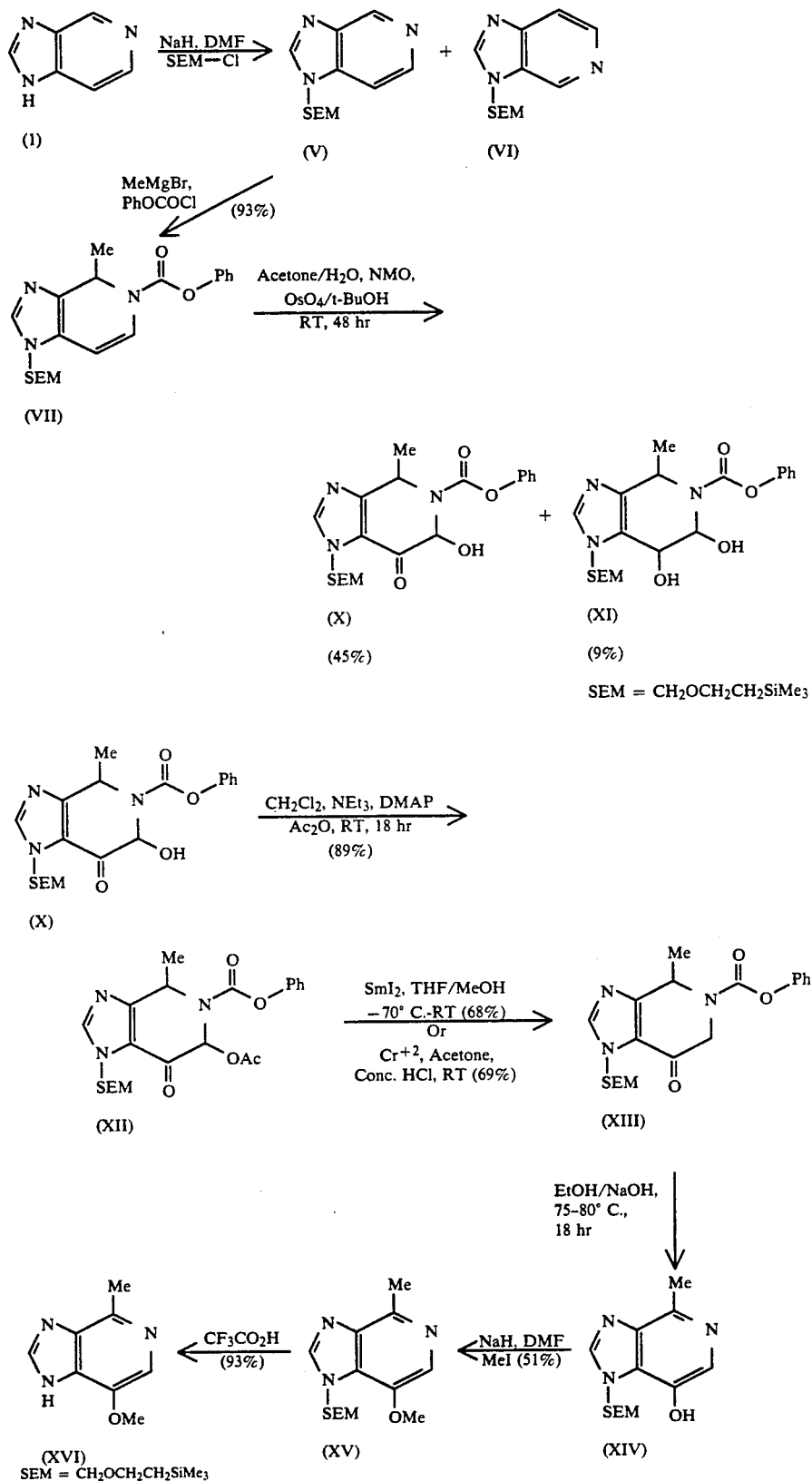
SEM = CH₂OCH₂CH₂SiMe₃
Thus, the addition product VII (Schemes B and D), which is isolated on reacting V with phenyl chloroformate and methyl magnesium bromide, is treated with osmium tetroxide in aqueous acetone containing N- methylmorpholine-N-oxide at room temperature for 48 hours to give the diol XI and the hydroxyketone X. The hydroxyketone X is acetylated (acetic anhydride, DMAP methylene chloride, room temperature, 24 hrs,) and the product XII is treated with $CrCl_2$ in acetone to give the deacetoxylated product XIII. Clevage of the carbamate XIII and air oxidation of the resulting product gave the N-1 protected 4-methyl-7-hydroxy imidazopyridine product XIV. The compound (XIV) is treated with NaH/DMF and then with iodomethane to give XV. Deprotection of product XV gave the 4-methyl-7-methoxy-imidazopyridine (XVI).

chloro group of 11 can easily be displaced by other nucleophiles such as alkoxide (OR), thioalkyl (SR), dialkylamino ($NR_2$) and the like to give a variety of compounds 12. Nitration of 11 or 12 using sulfuric acid/nitric acid gives the compound 13. Reduction Of 13 (e.g., using pd/C, H2 or Raney-Nickel) gives the 4-aminopyridine compound 14. When $R_7$ in 13 is SR, the reduction of nitro group may preferably be carried out using reagents such as triethylphosphine or $NaBH_4$/$NiCl_2$. Formation of nitramine 15 (using sulfuric acid, nitric acid, 0° C.) and its rearrangement to nitro-amino (using e.g., sulfuric acid) gives the derivative 16. The

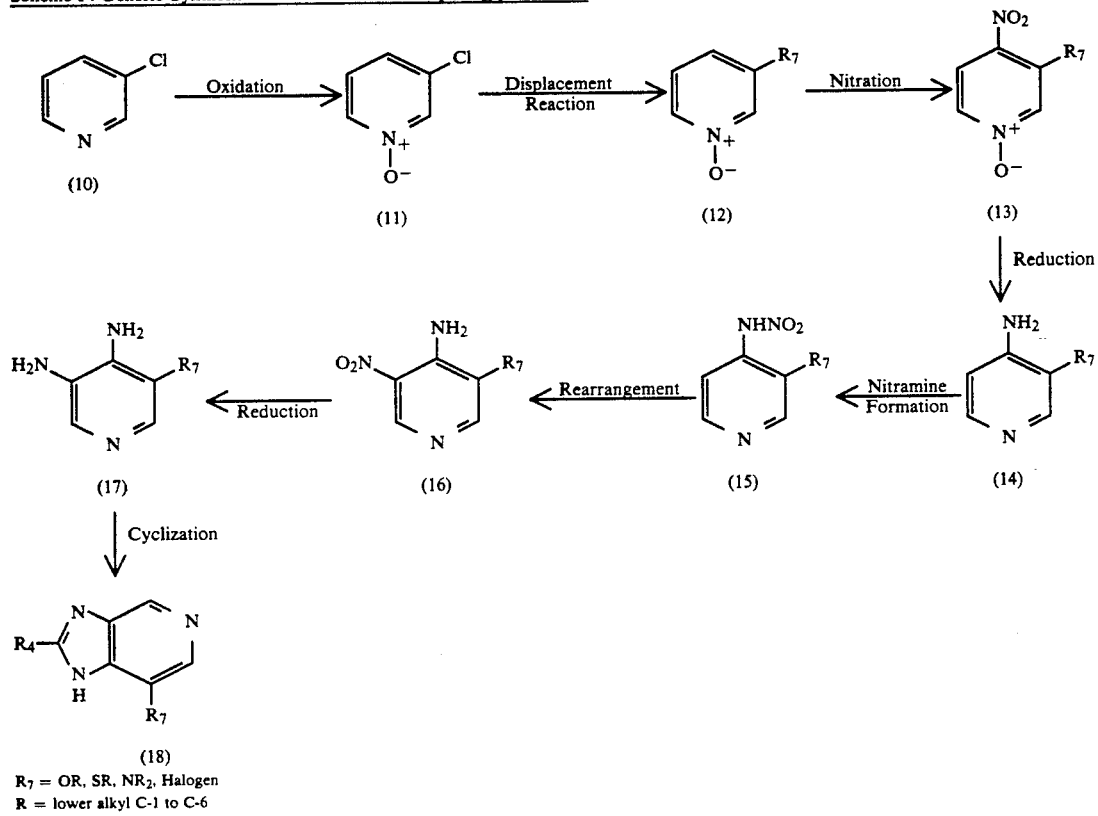

Scheme F: Generic Synthesis of 7-substituted imidazo[4,5-c]pyridines $R_7$ = OR, SR, $NR_2$, Halogen
R = lower alkyl C-1 to C-6

Synthesis of 7-substituted-imidazo[4,5-c]pyridines

The imidazo[4,5-c]pyridines of formula II wherein the $R_3$ group is substituted at position 7 of the pyridine ring can be prepared according to Scheme F. Commercially available 3-chloropyridine (10) is oxidized with reagents such as m-chloroperoxybenzoic acid or hydrogen peroxide to give the N-oxide intermediate (11). The nitro group is reduced again as described above and the resulting diamino compound 17 is cyclized by heating with a carboxylic acid ($R_4CO_2H$) in the presence of a mineral acid such as polyphosphoric acid or orthoester [($R_4C(OR)_3$)] in the presence of an acid catalyst such as p-toluenesulfonic acid to give the desired 7-substituted imidazopyridine 18.

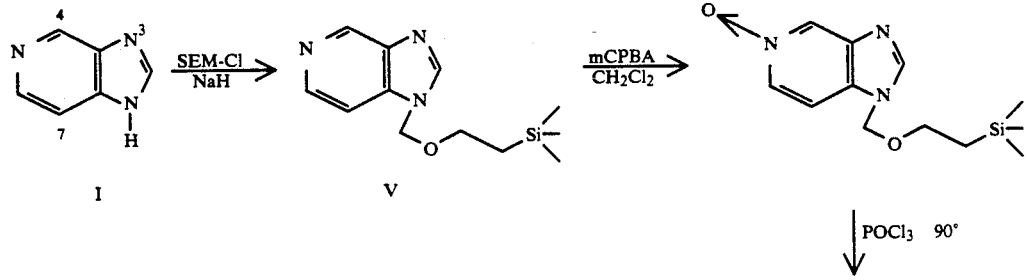

Scheme G: Synthesis of 4-chloro-imidazo[4,5-c]pyridine

Scheme G: Synthesis of 4-chloro-imidazo[4,5-c]pyridine

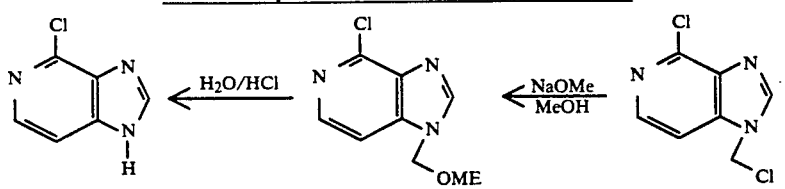

The imidazo[4,5-c]pyridine wherein $R_3$ (Formula II) is 4-chloro is prepared according to Scheme G starting with the imidazopyridine 1. Position 1 of this compound is protected by reaction with a 2-(trialkylsily) ethoxymethyl chloride and a base such as sodium hydride or potassium hydride in a polar aprotic solvent such as dimethylformamide. Typically, the reaction is carried out at room temperature. The protected imidazopyridine is reacted with m-chloroperbenzoic acid in methylene chloride at room temperature to give the pyridine N-oxide product. The N-oxide product is heated in $POCl_3$ at temperatures up to 90° C. to give 4-chloro-1-chloromethyl imidazopyridine. Treatment of this compound with sodium methoxide in methanol gives the 4-chloro-1-methoxymethyl imidazopyridine. Reacting this compound with aqueous acid with heating gives the 4-chloro-imidazo[4,5-c]pyridine.

Scheme H. The imidazo[4,5-c]pyridine (1) is protected at N-1/N-3 to give 2 as discussed in Scheme A. The product 2 is oxidized using e.g., hydrogen peroxide, 3-chloroperoxybenzoic acid to give the N-oxide intermediate 19. Rearrangement of 19 on heating with reagents such as acetic acid, trifluoroacetic acid gives the pyridone derivative 20. The intermediate 20 is treated with base such as sodium hydride, potassium hydride in polar aprotic solvent such as DMF, dimethylacetamide and alkylated by reaction with substituted benzyl halide to give 21. The protected group ($R_5$) at N-1/N-3 from 21 is removed by using the appropriate conditions as discussed in Scheme A. The resulting 5-substituted-4-hydroxy derivative 22 is alkylated after generating the anion [with e.g., sodium hydride, potassium hydride, potassium tert-butoxide or sodium bis(trimethylsilyl)amide] and reacting with alkyl halide ($R_8X$) to give the

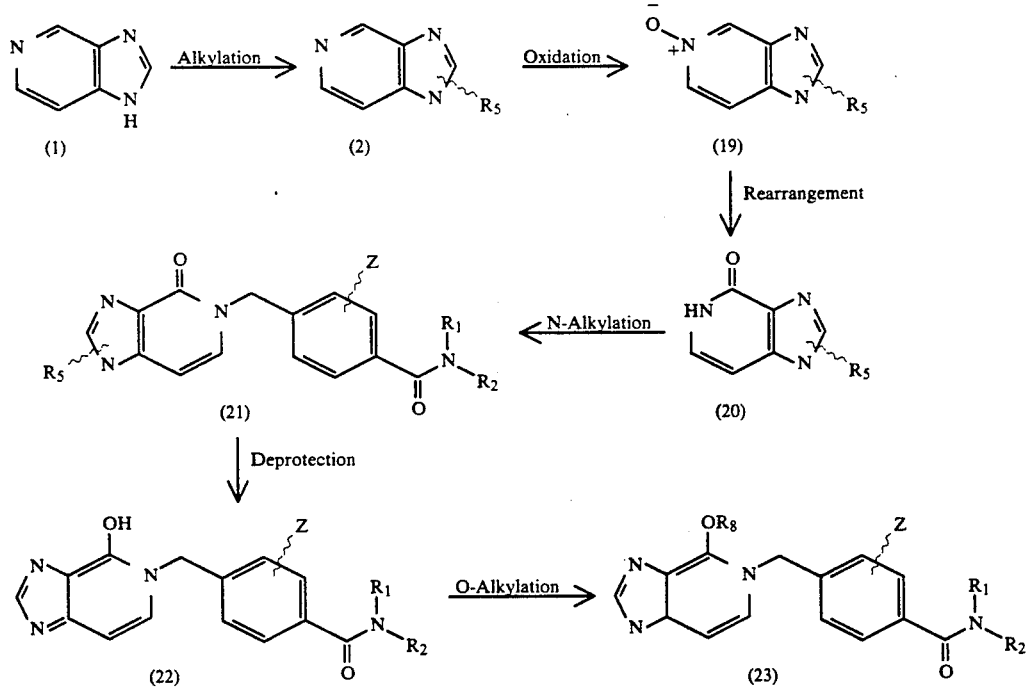

Scheme H: General Synthesis of 4-OH and 4-OAlkyl Imidazopyridine Analogs

Synthesis of 4-OH and 4-Oalkyl-imidazo[4,5-c]pyridine analogs

The synthesis of 4-OH and 4-Oalkyl-imidazo[4,5-c]pyridine analogs can be accomplished as shown in target 4-Oalkyl analogs 23.

Scheme I:
Synthesis of 4-OH and 4-OMe imidazopyridine Analogs

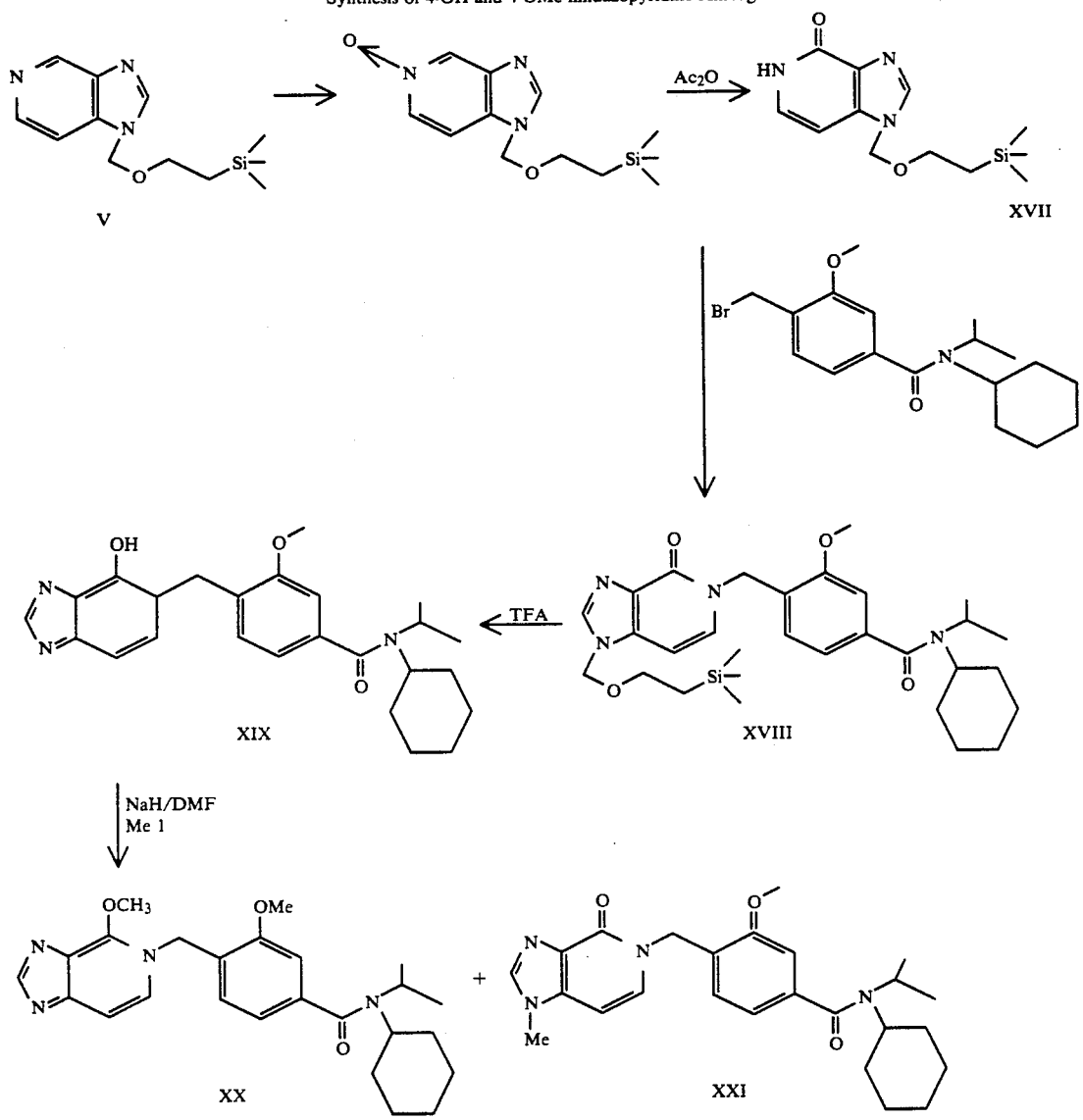

Imidazo[4,5-c]pyridine is protected at N-1 by SEM-Cl and converted to a pyridine N-oxide using m-chloroperbenzoic acid in a manner described for the preparation of 4-chloro-imidazo[4,5-c]pyridine (Scheme G). The pyridine-N-oxide compound is refluxed in acetic anhydride for 4 hrs. to give 4-oxo-1-(2-trimethylsilyl)ethoxymethyl-imidazo[4,5-c]pyridine (XVII). Reacting this compound with 4-bromomethyl-3-methoxy-benz-[N-isopropyl, N-cyclohexyl)amide and sodium hydride in dimethylformamide at room temperature for 4 hours gives the 5-benzylated product (XvIII). Clevage of the SEM-group is accomplished by trifluoro-acetic acid at 50° C. for 18 hours to give the compound XIX (titled compound). Treatment of the 4-hydroxy group of the compound with sodium hydride and iodomethane gives the compound XX (titled compound).

The haloalkyl benzamides are prepared according to the following reaction Scheme J

Scheme J

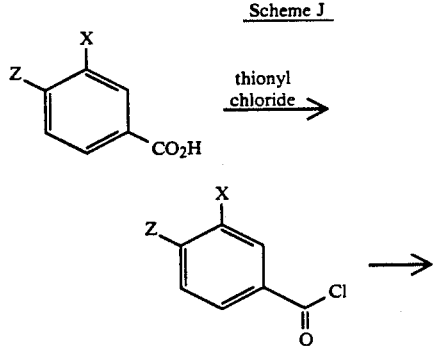

-continued
Scheme J

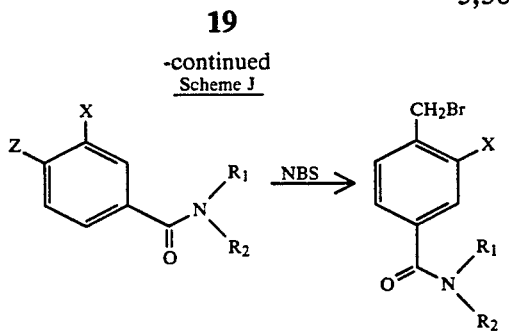

Scheme K

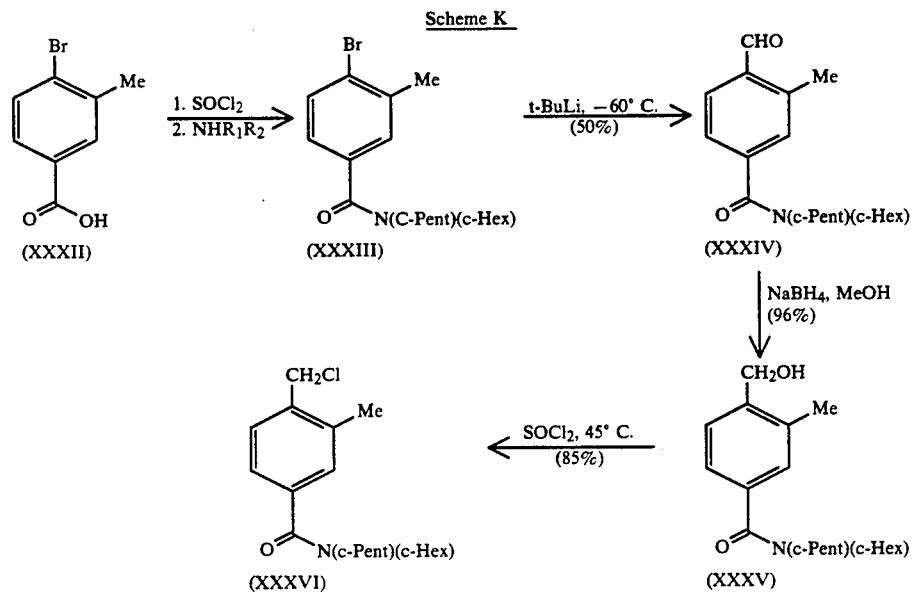

wherein $R_1$ and $R_2$ are defined as before; Z is $CH_2Br$, $CH_3$ or H; X is H, fluoro, OMe or methyl Thus according to the above scheme the acid chlorides are prepared from the corresponding carboxylic acids by treatment with excess thionyl chloride at temperatures of from room temperature to reflux. Excess thionyl chloride is removed by azeotrope with toluene. The residual acid chloride is dissolved in THF and cooled to $-10°$ C. A solution of two molar equivalents of the secondary amine in THF is added dropwise with stirring. When addition is completed, the reaction is allowed to warm to room temperature and stirred for 1-2 hours. The reaction is quenched with 1N HCl, diluted with $H_2O$ and extracted three times with ethyl acetate. The combined organic layers are washed with saturated aqueous sodium bicarbonate solution, with water and with saturated aqueous sodium chloride and dried over sodium sulfate. The drying agent is filtered and the filtrate concentrated in vacuo to give a crude product that was chromatographed on silica gel using mixtures of ethyl acetate and hexane to give the purified amide.

When Z is $CH_2Br$ and X is H, the above description is sufficient for the preparation of the compounds of Formula III. When Z is $CH_3$, and X is OMe or F, or when Z is H, and X is $CH_3$, then the amide in the scheme above must be treated with a halogenating agent such as N-bromosuccinimide.

For example, a stirred mixture of the purified amide and NBS (1:1 molar ratio) in carbon tetrachloride is irradiated with a sun lamp (150 or 275 W) for 1-3 hours. A white precipitate is filtered and washed with a minimum amount of $CHCl_3$. The filtrate is washed with water and the aqueous layer, after basification with ammonium hydroxide, is extracted three times with chloroform. All organic layers are combined, washed three times with saturated aqueous sodium chloride solution and dried over sodium sulfate.

The drying agent is filtered and the filtrate concentrated in vacuo to give a crude product that is chromatographed on silica gel using mixtures of ethyl acetate and hexane to give the purified bromomethyl compound.

Compounds where W of formula III is substituted with methyl is synthesized from 4-bromo-3-methyl-benzoic acid (XXXII) as shown in Scheme K. The benzoic acid is converted to substituted benzamide (XXXIII) by forming acid chloride and reacting with appropriate amine as discussed above. The bromobenzene derivative (XXXIII) is treated with an organometallic reagent such as t-butyl lithium and reacted with an electrophile such as dimethylformamide. The resulting aldehyde (XXXIV) is reduced to alcohol (XXXV) with a reducing agent such as sodium borohydride and the hydroxy group converted to a leaving group such as chloro by reacting with thionyl chloride to yield the desired compound (XXXVI).

Scheme L
Synthesis of 2-Alkoxy-4-Halomethyl Benzoic Acid Amide

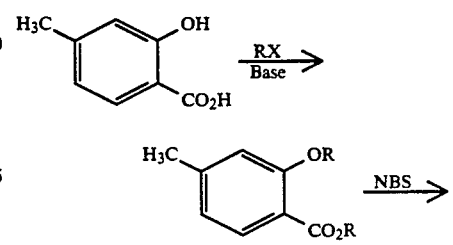

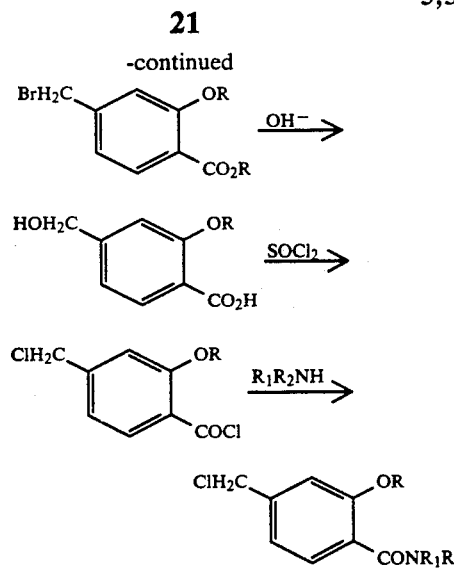

Scheme M

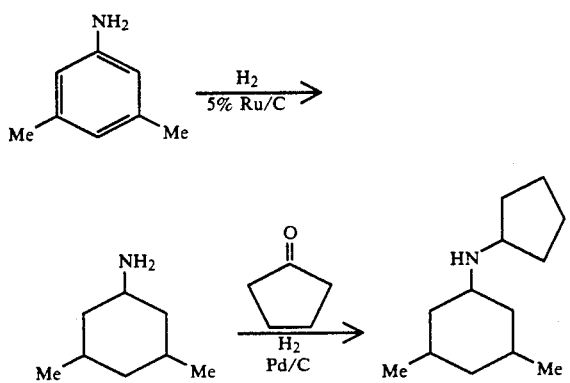

2-Alkoxy-4-chloromethylbenzoic acid amides may be synthesized according to the sequence shown in Scheme L. The starting 2-hydroxy-4-methyl benzoic acid was converted to the 2-alkoxy ester using an alkyl halide such as methyl iodide in the presence of a base such as potassium carbonate in a solvent such as dimethylformamide at temperatures ranging from room temperature to 60°. The 2-alkoxy ester is brominated using a free radical brominating agent such as N-bromosuccinimide in the presence of a free radical initiator such as a sun lamp. The resultant 4-bromomethyl carboxylic acid ester is saponified to the acid with concomitant displacement of the benzylic bromide to give the 2-alkoxy-4-hydroxymethyl benzoic acid using a base such as potassium hydroxide in water at temperatures ranging from 80° to ≦100°. The use of an organic co-solvent is permissible in order to facilitate dissolution of the organic substrate. Suitable cosolvents are dioxane or tetrahydrofuran. The hydroxymethyl derivative is converted to the 4-chloromethyl-2-alkoxybenzoyl chloride derivative by reaction with a chlorinating agent such as thionyl chloride at temperatures ranging from room temperature to 79°. The acid chloride is then converted to the amide by reaction with the appropriate amine in a solvent such as tetrahydrofuran in the presence of a tertiary amine such as triethylamine to act as a hydrochloric acid scavenger. Temperatures may range from 0° to 60°.

N-cis, cis-3,5-Dimethylcyclohexyl-N-cyclopentyl amine is synthesized as shown in Scheme M. 3,5-Dimethylcyclohexyl amine is synthesized by catalytic hydrogenation of 3,5-dimethyl aniline for 7 to 24 hours. A suitable catalyst is 5% ruthenium on carbon. Hydrogenation pressure may change from 500 to 1500 psi and temperatures may range from 80° to 150°. N-cis cis-3,5-Dimethylcyclohexyl-N-cyclopentyl amine is formed by reductive amination of cyclpentanone with 3,5-dimethylcyclohexyl amine. The reductive amination may be carried out by hydrogenation using palladium on carbon as catalyst at pressures ranging from 15 to 90 psi. The temperature may range from room temperature to 50°. The reaction time is from 7 to 48 hours.

The additional secondary amines may be prepared by any number of methods known to those skilled in the art. See references Emerson, W. S. Org. Reactions 4, 174 1948)

J. B. Cambell, L. B. Lavaginino in "Catalysis in Organic Syntheses" (Jones W. H., ed.) p. 43, Academic Press, New York, 1980.

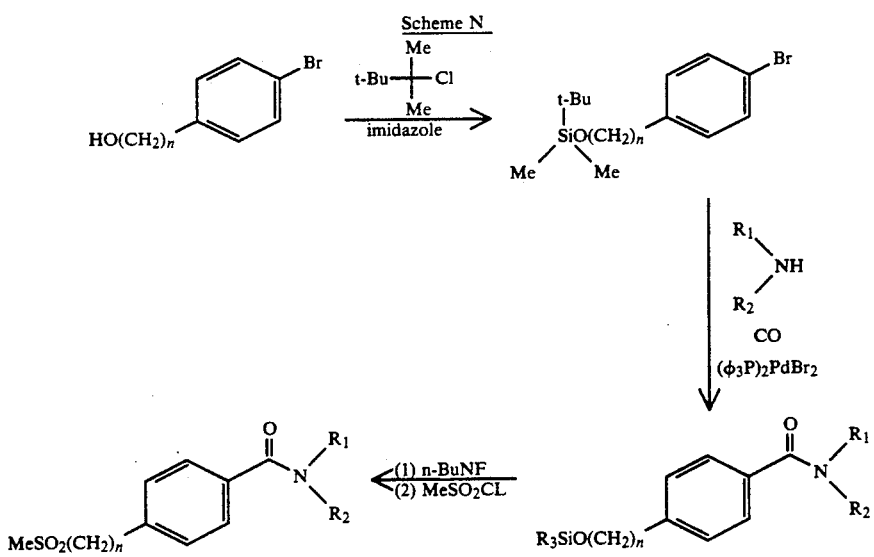

Scheme N

The benzamides of Formula III wherein n is 2 or 3 can be prepared according to the Scheme N starting with the appropriate hydroxyalkyl bromobenzene. The hydroxyl group is protected as a trialkylsilyl ether by reaction with a trialkylsilyl chloride and imidazole in a suitable solvent such as dimethylformamide. An example of such a protecting group would be the t-butyldimethylsilyl ether. The crude silyl ether is purified by chromatography on silica gel using mixtures of ethyl acetate and hexane. The aryl bromide is converted to the carboxamide according to the procedure of Schoenberg et al. [J. Org. Chem., 39, 3327(1974)]. Thus, the aryl bromide is reacted with carbon monoxide in the secondary amine as solvent using bistriphenylphosphine palladium(II) dibromide as catalyst at about 100° C. for 8–26 h. in a pressure vessel. The reaction vessel is vented, the reaction mixture triturated with ethyl ether and the washings filtered. The filtrate is washed with 10% aqueous HCl, water and brine. After drying over a suitable drying agent, such as magnesium sulfate, and filtering, the filtrate is concentrated and the residue chromatographed on silica gel using mixtures of ethyl acetate and hexane as eluent to give pure product. The silyl ether is removed by reaction with tetra-n-butylammonium fluoride and the alcohol is converted to a sulfonate ester by reaction with an alkyl or arylsulfonyl chloride. An example of such a sulfonate would be the methanesulfonate.

starting material. This is converted to the amide 20 by first converting acid 19 to the acid chloride by contact with agents such as oxalyl chloride or thionyl chloride and then treating the acid chloride with the desired amine. Amide 20 is converted to the benzylic halide 21 by treatment with a halogenating agent such as N-bromosuccinimide. Halide 21 is versatile and in addition to serving as an intermediate to alkoxyalkyl compounds, is also an intermediate to alkylthioalkyl and alkylaminoalkyl compounds by treatment with the appropriate Z derivative. When halogen is displaced with a metal alkoxide, such as sodium methoxide, the methoxymethyl derivative (22. Z is OMe) is obtained. Conversion of 22 (Z is OMe) to aldehyde 23 (Z is OMe) is effected by controlled reduction with a reducing agent such as diisobutylaluminum hydride, followed by acid hydrolysis. Reduction of aldehyde 23 to alcohol 24 is effected by a second reduction with another reducing agent such as sodium borohydride or lithium tri-t-butoxyaluminum hydride. Alcohol 24 is converted to a derivative suitable for nucleophilic displacement such as 25 where Z' is a leaving group such as halide or aryl or alkyl sulfonate. Such conversion is effected by treatment of 24 with, for example, p-toluenesulfonyl chloride, methanesulfonyl chloride, or thionyl chloride.

Compounds where W of formula III is substituted

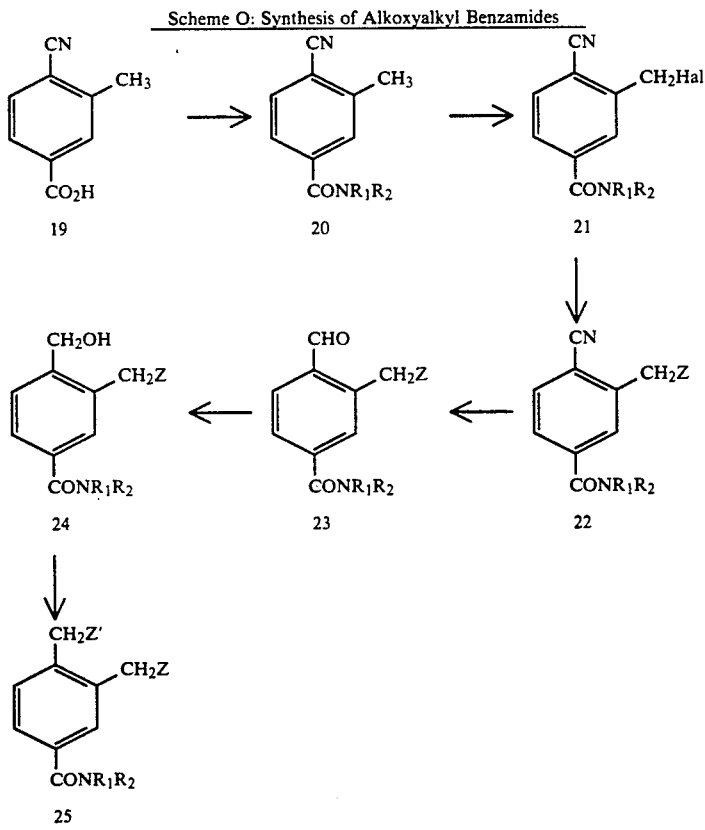

Scheme O: Synthesis of Alkoxyalkyl Benzamides

In Scheme O $R_1$ and $R_2$ are defined as before; "Hal" is halogen; Z is alkoxy, thioalkyl, alkyl and dialkylamino; and Z' is chloro, bromo, alkanesulfonyloxy, arylsulfonyloxy or p-toluenesulfonyloxy.

When W of Formula III is substituted with alkoxyalkyl, such substitution may be carried out by methods known to those skilled in the art. Such a method might, for example, employ the substituted benzoic acid 19 (F. Fichter, G. Shetty, Helv. Chim. Acta, 20, 563 (1937)) as with hydroxy can be made from the corresponding methoxy substituted compounds by treatment with a demethylating reagent such as lithium ethyl mercaptide in a dipolar, aprotic solvent such as dimethylformamide at temperatures ranging from room temperature to 200° C.

Preparation of 2-Methoxy-4-bromomethyl-5-bromobenz-(N-cyclopentyl,N-2-methylcyclohexyl)amide

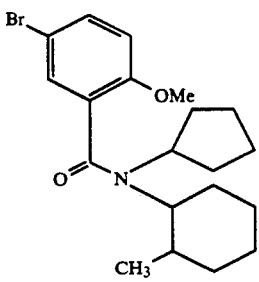

The above compound is prepared from 2-methoxy-4-methylbenz(N-cyclopentyl,N-2-methyl-cyclohexyl)amide and N-bromo succinimide in carbon tetrachloride by irradiation with a sun lamp for 5 hours.

Preparation of 3-Bromo-4-(bromomethyl)-N-cyclohexyl-N-cyclopentyl-2,6-dimethoxybenzamide

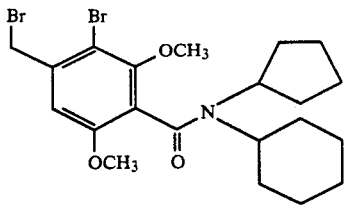

The above compound is prepared from 2,6-dimethoxy-4-methyl benzoic acid described by I. W. Mathison, R. C. Gueldner, D. M. Carroll, J. Pharma Sci 57 1820, (1968). The substituted benzoic acid is converted to the corresponding amide by first converting said compound to the acid chloride (using thionyl chloride) followed by condensation with N-cyclohexyl,N-cyclopentylamine. Irradiation of 2,6-dimethoxy-4-methyl-benz(N-cyclohexyl, N-cyclopentyl)amide in the presence of N-bromosuccinimide following the procedure described for the preparation 2-methoxy-4-bromomethyl-5-bromobenz-N-cyclopentyl,N-(2 methylcyclohexyl)amide gives two products 2,6-dimethoxy-3-bromo-4-methylbenz-(N-cyclohexyl,N-cyclopentyl)amide and 2,6-dimethoxy-3-bromo-4-bromomethylbenz(N-cyclohexyl,N-cyclopentyl) amide.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal, infusion techniques or intraperitoneally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is selected in accordance with a variety of factors, including the type, age, weight, sex and medical condition of the patient; the severity of the infection; the route of administration; and the particular compound employed and thus may vary widely.

Dosage levels of the order from about 0.01 mg to about 100 mg per kilogram of body weight per day are useful in the treatment of the above-indicated conditions (from about 0.5 mg to about 5 gs. per patient per day). Preferably, from about 0.01 mg to about 50 mg per kilogram of body weight per daily dosage produces highly effective results (about 0.5 mg to about 2.5 gm per patient per day).

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules which may be taken singlely or multiply. These may with advantage contain an amount of active ingredient from about 0.5 to 250 mg preferably from about 0.5 to 150 mg. A suitable daily dose for a mammal may vary widely depending on the condition of the patient and other factors. However, a dose of from about 0.01 to 100 mg/kg body weight, particularly from about 0.01 to 75 mg/kg body weight may be appropriate.

The active ingredient may also be administered by injection as a composition wherein, for example, saline, dextrose or water may be used as a suitable carrier. A suitable daily dose is from about 0.01 to 100 mg/kg body weight injected per day in single or multiple doses or continuous infusion depending on the disease being treated. A preferred daily dose would be from about 0.01 to 50 mg/kg body weight.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The amount of active ingredient that may be combined with the carrier materials to produce a single dosage form which may be taken singlely or multiply will vary depending upon the host treated and the particular mode of administration. For example, a formulation intended for the oral administration of humans may contain from 0.5 mg to 250 mg of active agent compounded with an appropriate and convenient amount of carrier material which may vary from about 5 to 95 percent of the total composition. Dosage unit forms will generally contain between from about 0.5 mg to about 150 mg of active ingredient.

The following Examples are intended to further illustrate the present invention and not to limit the invention in spirit or scope. In the Examples, all parts are parts by weight unless otherwise expressly set forth.

EXAMPLE 1

Preparation of
5-[4-(N-methyl-N-cyclohexylcarboxamido) benzyl]imidazo4.5-c]pyridine

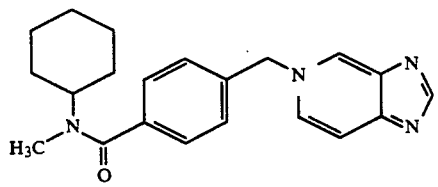

To a stirred solution of imidazopyridine (5.86 g, 49.2 mmol) in DMF (125 ml) under a nitrogen atmosphere was added washed, dried sodium hydride (prepared from 3.54 g of 50% dispersion in oil by washing four times with 50–75 ml portions of hexane). After stirring for 1 hr at room temperature, the evolution of hydrogen gas had ceased and the reaction was cooled to −10° C. N-Methyl-N-cyclohexyl-α-bromo-p-toluic acid amide (16.9 g, 54.5 mmol) was added. The reaction was stirred at 0° for 45 min. and at room temperature for 3 hrs.

DMF was removed in vacuo and the residue was diluted with H$_2$O (200 ml) and the resulting solution was saturated with sodium chloride. The aqueous solution was extracted four times with ethyl acetate (100 ml portions) and the combined organic layers were washed three times with saturated aqueous sodium chloride solution (150 ml portions). After drying over sodium sulfate, the organic solution was filtered and concentrated in vacuo to give 13.38 g of crude product as a brown gum. This material was chromatographed on silica gel using ethanol/chloroform/ammonium hydroxide (20/79/1) to give 3.13 g of compound as an orange oil that crystallized on treatment with ethyl acetate. Recrystallization from ethyl acetate yielded 1.06 g. The resulting product had the following properties:

Analysis Calcd for C$_{21}$H$_{24}$N$_4$O. ¼ H$_2$O: C, 71.46; H, 7.00; N, 15.88. Found: C, 71.14; H, 7.18; N, 15 78 m.p. 115–17° C.

EXAMPLE 2

Preparation of 5-[4-(N-methyl-N-cyclohexylcarboxamido)-2-fluorobenzyl]imidazo[4,5-c]pyridine

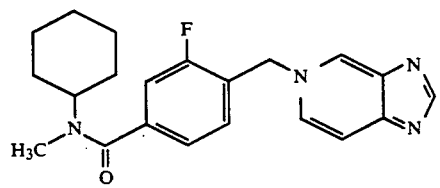

A solution of N-methyl, N-cyclohexyl 3-fluoro 4-bromomethyl benzamide (1.2 g 2.66 mm) and imidazopyridine (0.48 g, 4.0 mmol) in dimethylacetamide (25 ml) was heated overnight at 70–80° C. with stirring under N$_2$. Reaction solvent was removed in vacuo and the residue diluted with water and basified with ammonium hydroxide. The aqueous solution was extracted four times with chloroform and the combined organic extracts were backwashed three times with saturated aqueous sodium chloride solution. The organic solution was dried over magnesium sulfate. The drying agent was filtered and the filtrate concentrated in vacuo to give 0.88 g of the crude product. Purification of the compound was effected by chromatography on silica using mixtures of chloroform, ethanol and ammonium hydroxide. The resulting product had the following properties: Analysis calcd for C$_{21}$H$_{23}$FN$_4$O 0.8 H$_2$O: C,66.22; H,6.51; N,14.71; F,4.99. Found: C,66.03; H,6.44; N,14.65; F,4.91. m.p. 154–158° C.

In the same manner as described in Example 2 the compounds of the Examples 3 to 11 described in Tables A & B were prepared.

TABLE A

[Structure: imidazopyridine with R3, R4 substituents, N-(CH2)n linker to phenyl bearing X and C(O)NR1R2]

| Example | R1 | R2 | X | n | R3 | R4 | M pt (°C.) | Analysis Calcd. | Found | Molecular Formula |
|---------|-----|-----|------|---|----|----|-----------|-----------------|-------|-------------------|
| 3 | cyclopentylmethyl | cyclopentyl | OCH3 | 1 | H | H | 217–19 | C 71.12<br>H 7.26<br>N 13.28 | 70.83<br>7.33<br>13.06 | $C_{25}H_{30}N_4$<br>$0.2H_2O$ |
| 4 | cyclohexylmethyl | cyclopentyl | OCH3 | 1 | H | H | 197–99 | C 71.01<br>H 7.52<br>N 12.74 | 70.87<br>7.49<br>12.70 | $C_{26}H_{32}N_4O$<br>$0.4H_2O$ |
| 5 | cyclohexylmethyl | isobutyl | OCH3 | 1 | H | H | 192–95 | C 70.90<br>H 7.44<br>N 13.78 | 70.75<br>7.47<br>13.71 | $C_{24}H_{30}N_3O$ |
| 6 | cyclohexylmethyl | CH3 | OCH3 | 1 | H | H | 206–08 | C 69.15<br>H 6.86<br>N 14.67 | 68.78<br>6.88<br>14.57 | $C_{22}H_{26}N_4O$<br>$0.2H_2O$ |
| 7 | cyclohexylmethyl | cyclopentylmethyl | F | 1 | H | H | 205–08 | C 71.14<br>H 6.95<br>N 13.33<br>F 4.52 | 71.11<br>7.11<br>13.16<br>4.30 | $C_{25}H_{29}FN_4O$<br>$0.1H_2O$ |
| 8 | cyclohexylmethyl | isobutyl | F | 1 | H | H | 178–82 | C 68.46<br>H 6.79<br>N 13.89<br>F 4.71 | 68.46<br>6.71<br>13.45<br>4.38 | $C_{23}H_{27}FN_4$<br>$0.5H_2O$ |
| 9 | cyclohexylmethyl | CH3 | F | 1 | H | H | 154–8 | C 66.22<br>H 6.51<br>N 14.71<br>F 4.99 | 66.03<br>6.44<br>14.65<br>4.91 | $C_{21}H_{23}N_4F$<br>$0.8H_2O$ |

TABLE B

[Structure: imidazopyridine-N-(CH2)-phenyl-C(O)NR1R2]

| Example | R1 | R2 | M pt (°C.) | Analysis Calcd. | Found | Molecular Formula |
|---------|-----|-----|-----------|-----------------|-------|-------------------|
| 10 | cyclohexyl | —CH3 | 167–69 | C 72.38<br>H 6.94<br>N 16.08 | 72.26<br>7.10<br>16.01 | $C_{21}H_{24}N_4O$ |

TABLE B-continued

| Example | R₁ | R₂ | M pt (°C.) | Analysis Calcd. | Found | Molecular Formula |
|---|---|---|---|---|---|---|
| 11 | cyclohexylmethyl | isobutyl | 209-12 | C 73.37<br>H 7.50<br>N 14.88 | 72.97<br>7.63<br>14.61 | $C_{23}H_{28}N_4O$ |

EXAMPLE 12

Preparation of 5-[(4-(N,N-dicyclohexylcarboxamido)benzyl]imidazo[4,5-c]pyridine

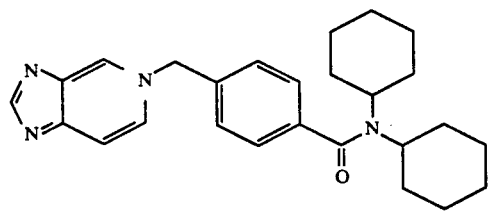

To a stirred solution of imidazopyridine (750 mg, 6.3 mmol) in N,N-dimethylacetamide, 4-bromomethyl-N,N-dicyclohexyl benzamide (2.6 g, 6.88 mmol) was added. The reaction mixture was stirred under argon at 80-85° C. After 24 h, the reaction flask was cooled to room temperature and the solvent removed under reduced pressure at <45° C. The residue obtained was triturated with ether (2×70 mL) and filtered. The crude product (2.7 g) was chromatographed (silica gel, $CH_2Cl_2$-MeOH-$NH_4OH$ 80-20-1) to give pure product (1.47 g, 62%) which was recrystallized from EtOAc-$CH_3CN$. The resulting product had the following properties: mp 233-35° C.; Analysis calcd. for $C_{26}H_{32}N_4O \cdot 0.3$ $H_2O$: C 74.0: H, 7.73: N, 13.28. Found C, 73.93; H, 7.90; N, 13.07.

In the same manner as described in Example 12 the compounds of the Examples 13 to 38 described in Table C were prepared.

TABLE C

| Example | R₁ | R₂ | X | n | R₃ | R₄ | M pt (°C.) | Analysis Calcd. | Found | Molecular Formula |
|---|---|---|---|---|---|---|---|---|---|---|
| 13 | cyclohexylmethyl | CH₃ | H | 1 | H | H | 115-17 | C 71.46<br>H 7.00<br>N 15.88 | 71.14<br>7.18<br>15.78 | $C_{21}H_{24}N_4O$<br>$0.25H_2O$ |
| 14 | —(CH₂)₇CH₃ | H | H | 1 | H | H | 113-15 | C 72.52<br>H 7.69<br>N 15.38 | 72.26<br>7.72<br>15.28 | $C_{22}H_{28}N_4O$ |
| 15 | —(CH₂)₉CH₃ | H | H | 1 | H | H | 141-45 | C 73.46<br>H 8.16<br>N 14.28 | 73.35<br>8.32<br>14.26 | $C_{24}H_{32}N_4O$ |
| 16 | cyclohexylmethyl | isobutyl | H | 1 | H | H | 209-10 | C 72.70<br>H 7.48<br>N 14.75 | 72.92<br>7.60<br>14.82 | $C_{23}H_{28}N_4O$<br>$0.2H_2O$ |
| 17 | cyclohexylmethyl | sec-butyl | H | 1 | H | H | 210-11 | C 73.80<br>H 7.69<br>N 14.35 | 73.40<br>7.78<br>14.25 | $C_{24}H_{30}N_4O$ |
| 18 | —(CH₂)₁₁CH₃ | H | H | 1 | H | H | 150-2 | C 74.28<br>H 8.57<br>N 13.33 | 74.10<br>8.75<br>13.36 | $C_{26}H_{36}N_4O$ |

TABLE C-continued

| Example | R₁ | R₂ | X | n | R₃ | R₄ | M pt (°C.) | Analysis Calcd. | Found | Molecular Formula |
|---|---|---|---|---|---|---|---|---|---|---|
| 19 | decahydronaphthyl | H | H | 1 | H | H | 113–28 | C 73.31<br>H 7.52<br>N 13.68 | 73.41<br>7.79<br>13.38 | C₂₅H₃₀N₄O<br>0.4H₂O |
| 20 | neopentyl-like | H | H | 1 | H | H | 221–2 | C 72.52<br>H 7.69<br>N 15.38 | 72.33<br>7.82<br>15.28 | C₂₂H₂₈N₄O |
| 21 | cyclohexylmethyl | CH₃ | H | 2 | H | H | 223–5 | C 71.15<br>H 7.27<br>N 15.09 | 70.79<br>7.48<br>14.81 | C₂₂H₂₆N₄O<br>0.5H₂O |
| 22 | cyclohexylmethyl | CH₃ | H | 3 | H | H |  | C 70.86<br>H 7.57<br>N 14.36 | 70.82<br>7.64<br>14.23 | C₂₃H₂₈N₄O<br>0.75H₂O |
| 23 | cyclopentyl | cyclopentylmethyl | H | 1 | H | CH₃ | 197–98 | C 74.62<br>H 7.46<br>N 13.93 | 74.24<br>7.50<br>13.80 | C₂₅H₃₀N₄O |
| 24 | cyclopentyl | cyclopentyl | H | 1 | CH₃ | H | 225–8 | C 72.31<br>H 7.48<br>N 13.18 | 72.36<br>7.57<br>13.50 | C₂₅H₃₀N₄O<br>0.7H₂O |
| 25 | cyclohexyl | cyclobutylmethyl | H | 1 | H | H | 190–3 | C 74.22<br>H 7.21<br>N 14.43 | 73.98<br>7.27<br>14.33 | C₂₄H₂₈N₄O |
| 26 | cyclohexyl | cyclopentylmethyl | H | 1 | H | H | 222–23 | C 74.62<br>H 7.46<br>N 13.93 | 74.21<br>7.45<br>14.26 | C₂₅H₃₀N₄O |
| 27 | cyclohexylmethyl | cyclohexylmethyl | H | 1 | H | H | 233–35 | C 74.0<br>H 7.73<br>N 13.28 | 73.93<br>7.90<br>13.07 | C₂₆H₃₂N₄O<br>0.3H₂O |
| 28 | cyclohexylmethyl | isobutenyl | H | 1 | H | H | 197–98 | C 73.84<br>H 7.69<br>N 14.35 | 73.86<br>7.87<br>14.35 | C₂₄H₃₀N₄O |

TABLE C-continued

| Example | R₁ | R₂ | X | n | R₃ | R₄ | M pt (°C.) | Analysis Calcd. | Analysis Found | Molecular Formula |
|---------|----|----|---|---|----|----|-----------|-----------------|----------------|-------------------|
| 29 | phenylmethyl | cyclopentylmethyl | H | 1 | H | H | 213–14 | C 75.73<br>H 6.10<br>N 14.13 | 75.66<br>6.18<br>14.08 | $C_{25}H_{24}N_4O$ |
| 30 | (3-methylcyclohexyl)methyl | cyclopentylmethyl | H | 1 | H | H | 187–89 | C 74.94<br>H 7.74<br>N 13.44 | 74.58<br>7.84<br>13.32 | $C_{26}H_{32}N_4O$ |
| 31 | (4-methylcyclohexyl)methyl | cyclopentylmethyl | H | 1 | H | H | 211–12 | C 74.94<br>H 7.74<br>N 13.44 | 74.85<br>7.84<br>13.39 | $C_{26}H_{32}N_4O$ |
| 32 | cyclohexylmethyl | isobutyl | H | 1 | H | H | 198–200 | C 73.84<br>H 7.69<br>N 14.35 | 73.20<br>7.70<br>14.74 | $C_{24}H_{30}N_4O$ |
| 33 | cyclohexylmethyl | 2-ethylbutyl | H | 1 | H | H | 211–13 | C 73.60<br>H 7.85<br>N 13.73 | 73.72<br>7.92<br>13.72 | $C_{25}H_{32}N_4O$<br>$0.2H_2O$ |
| 34 | cyclohexylmethyl | cyclopropylmethyl | H | 1 | H | H | 88–90 | C 72.06<br>H 7.04<br>N 14.62 | 72.25<br>7.16<br>14.48 | $C_{23}H_{26}N_4O$<br>$0.5H_2O$ |
| 35 | isopropyl | isopropyl | H | 1 | H | H | 224–5 | C 71.42<br>H 7.14<br>N 16.66 | 71.30<br>7.29<br>16.71 | $C_{20}H_{24}N_4O$ |
| 36 | cyclopentylmethyl | cyclopentylmethyl | H | 1 | H | H | 228–30 | C 74.22<br>H 7.21<br>N 14.43 | 74.04<br>7.29<br>14.28 | $C_{24}H_{28}N_4O$ |
| 37 | cyclohexylmethyl | H | H | 1 | H | H | 219–21 | C 70.33<br>H 6.68<br>N 16.41 | 70.34<br>6.87<br>16.28 | $C_{20}H_{22}N_4O$<br>$0.4H_2O$ |
| 38 | cyclohexylmethyl | —CH₂CH₃ | H | 1 | H | H | 156–8 | C 71.85<br>H 7.24<br>N 15.24 | 71.85<br>7.24<br>15.19 | $C_{22}H_{26}N_4O$<br>$0.3H_2O$ |

EXAMPLE 39

Preparation of
5-[4{-(N-cyclopentyl-3,5-dimethylcyclohexyl)carboxamido}benzyl]imidazo[4,5-c]pyridine

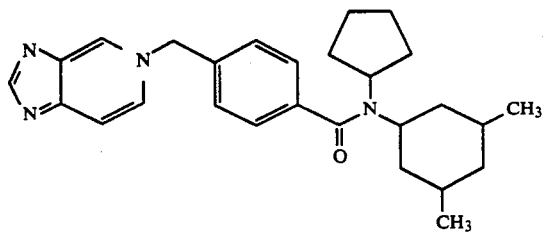

To a stirred solution of imidazopyridine (400 mg, 3.4 mmol) in N,N-dimethylacetamide (30 ml), 4-bromomethyl-N-cyclopentyl,N-3,5-dimethylcyclohexyl benzamide (1.4 g, 3.57 mmol) was added. The reaction mixture was stirred under argon at 80–85° C. After 40 h, the reaction flask was cooled to room temperature and the solvent removed under reduced pressure at <45° C. The residue obtained was triturated with ether (2×70 ml) and filtered. The crude (1.8 g) was chromatographed (silica gel, $CH_2Cl_2$-MeOH-$NH_4OH$ 90-10-1) to give pure product (1.05 g, 72%) which was recrystallized from EtOAc-$CH_3CN$. The resulting product had the following properties: mp 214–16° C. Anal calcd. for $C_{27}H_{34}N_4O$: C, 75.30; H, 7.9; N, 13.02. Found C, 74.92; H, 8.07; N, 12.97.

In the same manner as described in Example 39 the compounds of the Examples 40 to 55 described in Table D were prepared.

TABLE D

| Example | $R_1$ | $R_2$ | $R_3$ | $R_4$ | $R_5$ | $R_6$ | M pt (°C.) | Analysis Calcd. | Analysis Found | Molecular Formula |
|---|---|---|---|---|---|---|---|---|---|---|
| 40 | cyclopentyl-CH2 | 3-methylcyclopentyl | H | H | H | H | 204–6 | C 74.62<br>H 7.46<br>N 13.93 | 74.12<br>7.56<br>13.90 | $C_{25}H_{30}N_4O$ |
| 41 | isopropyl | 3-methylcyclopentyl | H | H | H | H | 229–31 | C 73.40<br>H 7.45<br>N 14.89 | 73.13<br>7.64<br>14.85 | $C_{23}H_{28}N_4O$ |
| 42 | cyclopentyl | 3,5-dimethylcyclohexyl | H | H | H | H | 214–16 | C 75.30<br>H 7.90<br>N 13.02 | 74.92<br>8.07<br>12.97 | $C_{27}H_{34}N_4O$ |
| 43 | cyclopentyl | 2-methylcyclohexyl | H | H | H | H | 223–5 | C 74.96<br>H 7.74<br>N 13.45 | 74.65<br>7.79<br>13.35 | $C_{26}H_{32}N_4O$ |
| 44 | cyclopentyl | norbornyl | H | H | H | H | 182–5 | C 75.00<br>H 7.31<br>N 13.46 | 74.72<br>7.35<br>13.37 | $C_{26}H_{30}N_4O$·$0.1H_2O_5$ |
| 45 | H | 6-methylpyridin-2-yl-methyl | H | H | H | H | 242–4 | C 66.79<br>H 5.26<br>N 19.47 | 66.79<br>4.97<br>19.26 | $C_{20}H_{17}N_5O$·$0.9H_2O$ |

TABLE D-continued

| Example | R₁ | R₂ | R₃ | R₄ | R₅ | R₆ | M pt (°C.) | Analysis Calcd. | Found | Molecular Formula |
|---|---|---|---|---|---|---|---|---|---|---|
| 46 | cyclopentylmethyl | 2-methyl-5-isopropylcyclohexyl | H | H | H | H | 95–103 | C 73.76<br>H 8.43<br>N 11.86 | 73.83<br>8.25<br>11.65 | C₂₉H₃₈N₄O<br>0.75H₂O |
| 47 | isopropyl | cyclohexyl | OCH₃ | H | H | OH | 235–37 | C 68.22<br>H 7.15<br>N 13.26 | 67.86<br>7.23<br>13.09 | C₂₄H₃₀N₄O₃ |
| 48 | isopropyl | cyclohexyl | OCH₃ | H | H | Cl | 171–3 | C 65.32<br>H 6.62<br>N 12.70<br>Cl 8.10 | 64.96<br>6.78<br>12.51<br>8.47 | C₂₄H₂₉N₄O₂Cl |
| 49 | isopropyl | cyclohexyl | OCH₃ | H | H | OCH₃ | 212–14 | C 66.71<br>H 7.50<br>N 12.40 | 66.53<br>7.25<br>12.26 | C₂₅H₃₂N₄O₃<br>0.75H₂O |
| 50 | cyclopentylmethyl | 3-methylcyclohexylmethyl | H | OCH₃ | H | H | 226–8 | C 72.60<br>H 7.67<br>N 12.54 | 72.28<br>7.65<br>12.44 | C₂₇H₃₄N₄O₂ |
| 51 | cyclopentylmethyl | 3-methylcyclohexylmethyl | OCH₃ | H | H | H | 186–8 | C 72.60<br>H 7.67<br>N 12.54 | 72.21<br>7.91<br>12.28 | C₂₇H₃₄N₄O₂ |
| 52 | cyclopentylmethyl | cyclohexylmethyl | OCH₃ | OCH₃ | H | H | 214–16 | C 69.29<br>H 7.45<br>N 11.97 | 69.01<br>7.42<br>11.86 | C₂₇H₃₄N₄O₃<br>0.3H₂O |
| 53 | cyclopentylmethyl | cyclohexylmethyl | Br | OCH₃ | OCH₃ | H | 191–3 | C 57.95<br>H 6.30<br>N 10.01<br>Br 14.3 | 67.56<br>6.01<br>9.93<br>15.8 | C₂₇H₃₃N₄O₃Br<br>1H₂O |
| 54 | cyclopentylmethyl | 2-methylcyclohexylmethyl | Br | H | OCH₃ | H | 167–70 | C 60.67<br>H 6.41<br>N 10.48<br>Br 14.95 | 60.47<br>6.24<br>10.00<br>14.57 | C₂₇H₃₅N₄O₂Br<br>0.5H₂O |

TABLE D-continued

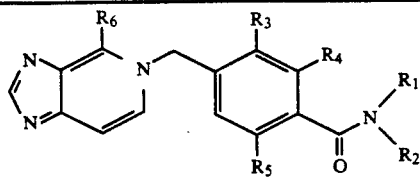

| Example | R₁ | R₂ | R₃ | R₄ | R₅ | R₆ | M pt (°C.) | Analysis Calcd. | Found | Molecular Formula |
|---|---|---|---|---|---|---|---|---|---|---|
| 55 | isopropyl | cyclohexyl | OMe | H | H | H | 210–13 | C 64.41<br>H 7.09<br>N 12.52<br>Cl 7.92 | 64.40<br>7.34<br>12.43<br>8.0 | $C_{24}H_{31}N_4ClO_2$<br>$0.25H_2O$ |

EXAMPLE 56

Preparation of 5-[4{-(N-isopropyl,N-3-methylcyclopentyl)carboxamido}benzyl]imidazo[4,5-c]pyridine

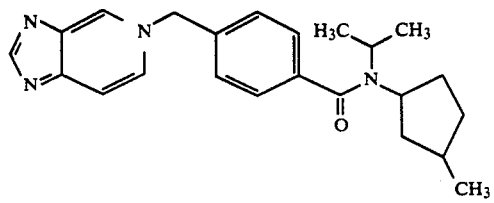

To a stirred solution of imidazopyridine (689 mg, 5.76 mmol) in N,N-dimethylacetamide (30 ml), 4-bromomethyl-N-isopropyl,N-3-methylcyclohexyl benzamide (2.17 g, 6.42 mmol) was added. The reaction mixture was stirred under argon at 95° C. After 48 h, the reaction flask was cooled to room temperature and the solvent removed under reduced pressure at <45° C. The residue obtained was triturated with ether (2×100ml) and filtered. The crude (2.97 g) was chromatographed (silica gel, $CH_2Cl_2$-MeOH-$NH_4OH$ 90-10-1) to give pure product (0.93 g, 43%) which was recrystallized from EtOAc-$CH_3CN$. The resulting product had the following properties: mp 229–31° C. Anal calcd. for $C_{23}H_{28}N_4O$: C, 73.40; H, 7.45; N, 14.89. Found C, 73.13; H, 7.64; N, 14.85.

EXAMPLE 57

Preparation of 5-[4{-(N-isopropyl,N-cyclohexyl)carboxamido}-2-methoxybenzyl]imidazo[4,5-c]pyridine

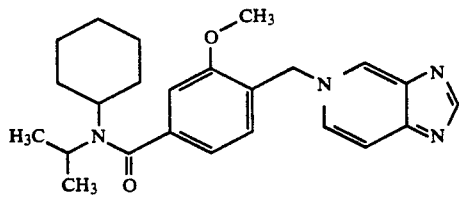

To a stirred solution of imidazopyridine (1.5 g, 12.6 mmol) in dimethylacetamide (120 ml) under argon, N-isopropyl,N-cyclohexyl-3-methoxy-4-bromomethyl benzamide (5.1 g, 13.86 mmol) was added in one portion. The reaction temperature was slowly raised to 80–85° C. and was stirred over the week-end. The reaction flask was cooled to room temperature and the solvent removed under reduced pressure at <45° C. The residue obtained was triturated with excess of dry ether (2×100 ml) and filtered. The crude product was chromatographed (silica gel; $CH_2Cl_2$:MeOH:$N_{H4}OH$::90:10:1) to give pure alkylated product (3.53 g, 69%). The product was recrystallized from ethyl acetate. The resulting product had the following properties: mp 192–95° C. Anal calcd. for $C_{24}H_{30}N_4O_2$:C, 70.90; H, 7.44; N, 13.78. Found C, 70.58; H, 7.43; N, 13.78.

EXAMPLE 58

Preparation of 5-4{-(N-isopropyl,N-cyclohexyl)carboxamido}-2-methoxybenzyl]-imidazo}4,5-c]pyridine hydrochloride

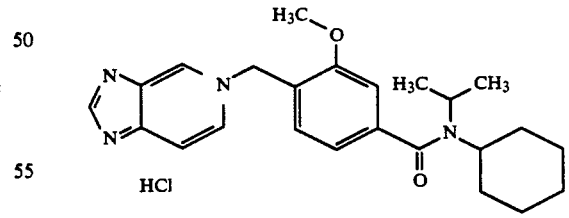

To a clear solution of the product of Example 57 (100 mg) in methanol (7 ml), HCl in dioxane (5 ml, 6N solution) was added. After stirring at room temp. for 2 h, the solvent was removed under reduced pressure. Ethyl acetate (25ml) was added and mixture was refluxed for 1 h. The contents were filtered hot and the residue was washed with more hot ethyl acetate. After drying, the product (92 mg) was collected. The resulting product had the following properties: mp 210–13° C. Anal calcd. for $C_{24}H_{31}N_4ClO_2$ 0.25 $H_2O$:C, 64.41; H, 7.09; N, 12.52; Cl, 7.92. Found C, 64.40; H, 7.34; N, 12.43, Cl, 8.0.

EXAMPLE 59

Preparation of
5-[4{-(N-cyclopentyl,N-3-methylcyclohexyl)carboxamido}-3-methoxybenzyl]imidazo[4,5-c]pyridine

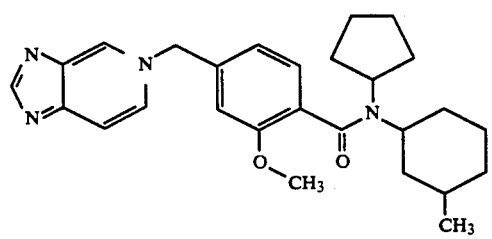

To a stirred solution of imidazopyridine (412mg, 3.47mmol) in N,N-dimethylacetamide (25 ml), 4-bromomethyl-2-methoxy-N-cyclopentyl, N-3-methylcyclohexyl benzamide (1.49g, 3.65 mmol) was added. The reaction mixture was stirred under argon at 90–95° C. After 48 h, the reaction flask was cooled to room temperature and the solvent removed under reduced pressure at <45° C. The residue obtained was triturated with ether (2×70ml) and filtered. The crude (1.85 g) was chromatographed (silica gel, $CH_2Cl_2$-MeOH-$NH_4OH$ 90-10-1) to give pure product (1.05 g, 67%) which was recrystallized from EtOAc. The resulting product had the following properties: mp 226–28° C. Anal calcd. for $C_{27}H_{34}N_4O_2$:C, 72.60; H, 7.67; N, 12.54. Found C, 72.28; H, 7.65; N, 12.44.

EXAMPLE 60

Preparation of
5-[4{-(N-cyclopentyl,N-3-methylcyclohexyl)carboxamido}-2-methoxybenzyl]imidazo[4,5-c]pyridine

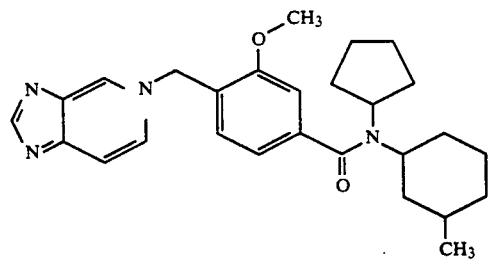

To a stirred solution of imidazopyridine (525 mg, 4.4 mmol) in N,N-dimethylacetamide (25 ml), 4-bromomethyl-3-methoxy-N-cyclopentyl, N-3-methylcyclohexyl benzamide (1.9 g, 4.66 mmol) was added. The reaction mixture was stirred under argon at 90–95° C. After 48 h, the reaction flask was cooled to room temperature and the solvent removed under reduced pressure at <45° C. The residue obtained was triturated with ether (2×100ml) and filtered. The crude was chromatographed (silica gel, $CH_2Cl_2$-MeOH-$NH_4OH$ 90-10-1) to give pure product (1.39 g, 71%) which was recrystallized from EtOAc-$CH_3CN$. The resulting product had the following properties: mp 186–88° C. Anal calcd. for $C_{27}H_{34}N_4O_2$:C, 72.60; H, 7.67; N, 12.54. Found C, 72.21; H, 7.91; N, 12.28.

EXAMPLE 61

Preparation of
5-[4{-(N-cyclopentyl,N-cyclohexyl)carboxamido}-2-methoxybenzyl]imidazo[4,5-c]pyridine

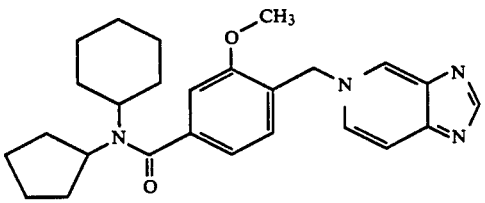

To a stirred solution of imidazopyridine (660 mg, 5.57 mmol) in N,N-dimethylacetamide (25 ml), 4-bromomethyl-2-methoxy-N-cyclopentyl,N-cyclohexyl benzamide (2.0 g, 5.07 mmol) was added. The reaction mixture was stirred under argon at 75° C. After 24 h, the reaction flask was cooled to room temperature and the solvent removed under reduced pressure. The residue obtained was diluted with water (650 ml) and basified with aq. ammonium hydroxide (20 ml). The reaction solution was extracted with chloroform (4×100 ml). The organic layer was washed with brine (3×250 ml), dried ($MgSO_4$) and filtered. The combined filtrate was concentrated and the residue (2.79 g) chromatographed (silica gel, $CHCl_3$-EtOH-$NH_4OH$ 10-90-1) to give desired product (1.36 g, 62%). The resulting product had the following properties: mp 197–99° C. Anal calcd. for $C_{26}H_{32}N_4O_2 \cdot 0.4 H_2O$:C, 71.01; H, 7.52; N, 12.74. Found C, 70.87; H, 7.49; N, 12.70.

EXAMPLE 62

Preparation of 5-[4{-(N-isopropyl,N-cyclohexyl)carboxamido}benzyl]imidazo[4,5-c]pyridine

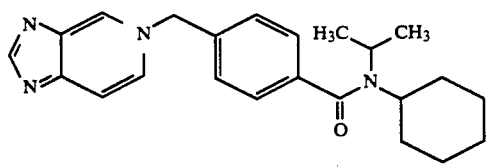

To a stirred solution of imidazopyridine (680 mg, 5.8 mmol) in N,N-dimethylacetamide (30 ml), 4-bromomethyl-N-isopropyl,N-cyclohexyl benzamide (2.2 g, 6.44 mmol) was added. The reaction mixture was stirred under argon at 80–85° C. After 20 h, the reaction flask was cooled to room temperature and the solvent removed under reduced pressure at <45° C. The residue obtained was triturated with ether and filtered. The crude (1.85 g) was chromatographed (silica gel, $CH_2Cl_2$-EtOH-$NH_4OH$ 80-20-1) to give pure product (1.29 g, 59%) which was recrystallized from EtOAc-$CH_3CN$. The resulting product had the following properties: mp 209–10° C. Anal calcd. for $C_{23}H_{28}N_4O \cdot 0.2 H_2O$: C, 72.70; H, 7.48; N, 14.75. Found C, 72.92; H, 7.60; N, 14.82.

EXAMPLE 63

Preparation of
5-[4-{(N-cyclohexyl,N-isopropyl)carboxamido}-2-methoxybenzyl]-4-chloro-imidazo[4,5-c]pyridine

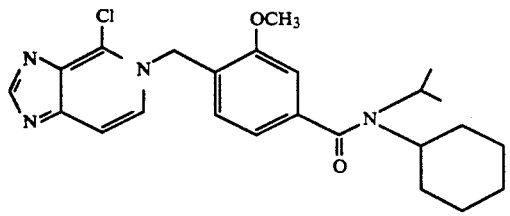

Preparation of the 4-chloro-imidazo [4,5-c]pyridine starting material as well as the N-cyclohexyl,N-isopropyl-2-methoxy-3-bromobenzoic acid amide have been described earlier in this specification (Scheme G). Coupling of the 4-chloro-imidazo[4,5-c]pyridine to the N-cyclohexyl,N-isopropyl-2-methoxy-3-bromobenzoic acid amide in dimethylacetamide at 85–90° for 26 h gives the titled compound.

EXAMPLE 64

Preparation of

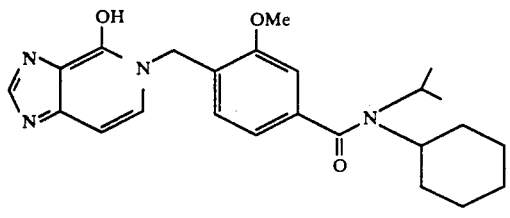

and

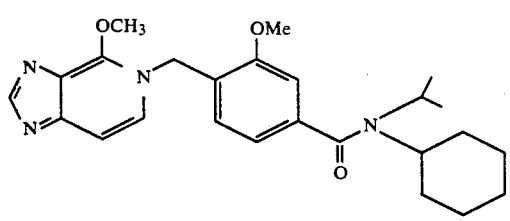

The above compounds can be synthesized according to Scheme I:

EXAMPLE 65

Preparation of
N-cyclopentyl-N-(3,5-dimethylcyclohexyl)-4-(5H-imidazo[4.5-c]pyridin-5-ylmethyl)-2-methoxybenzamide

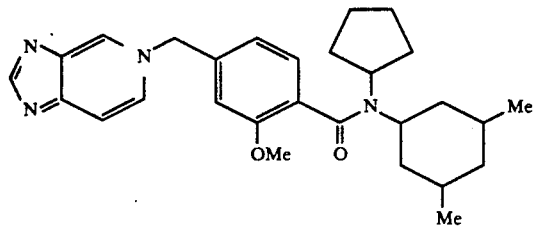

To a stirred solution of imidazopyridine (46 mg, 0.38 mmol) in N,N-dimethylformamide (10 mL), 4-bromomethyl-2-methoxy-N-cyclopentyl,N-3,5-dimethylcyclohexyl benzamide (162 mg, 0.38 mmol) was added. After stirring at room temperature for 18 hr, the solvent was removed under reduced pressure at <45° C. The residue was chromatographed (silica gel, $CH_2Cl_2$/MeOH/$NH_4OH$ 90/10/1) to give the title compound (143 mg, 78%). The resulting product has the following properties: mp 218-20° C. Anal calcd. for $C_{28}H_{36}N_4O_2 \cdot 1.3$ $H_2O$: C, 69.48; H, 8.04; N, 11.57. Found C, 69.46; H, 7.74; N, 11.51.

EXAMPLE 66

See Scheme K

Preparation of
N-cyclohexyl-4-formyl-3-methyl-N-(1-cylcopentyl)-benzamide

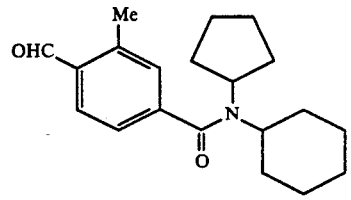

4-Bromo-3-methyl N-cyclopentyl, N-cyclohexyl amide (4 g, 0.011 moles) was dissolved in 40 mls of dry THF and cooled to −60°. t-Butylithium (13 mls of 1.7 M solution) was added and the reaction was stirred for 15 minutes under argon. DMF (804 mg) was added and the reaction mixture allowed to warm to 0° over 30 minutes. After stirring at 0° for 15 minutes, the reaction mixture was poured into 1N HCl and extracted with ethyl acetate. After drying the organic layer ($Na_2SO_4$) and removal of solvent, the residue was chromatographed on silica gel using 20% ethyl acetate/hexane as the eluent to give 1.75 g (50%) of the title product. m.p. 57–50° C. NMR (ppm, $CDCl_3$): 2.67 (3H, s); 7.21 (1H, s); 7.25 (1H, d, J=8 Hz); 7.82 (1H, d, J−8 Hz); 10.30 (1 h, s).

Preparation of
N-cyclohexyl-4-(hydroxymethyl)-3-methyl-N-(1-cyclopentyl)benzamide

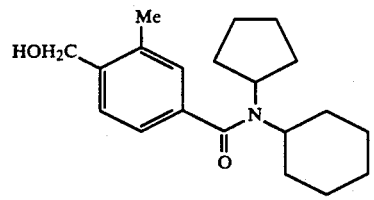

The aldehyde XXXIV of Scheme K (1.70 g, 0.0052 moles) was dissolved in 20 mls of MeOH and cooled to 0° C. under argon. $NaBH_4$ (110 mg) was added and the mixture was allowed to warm to 25° C. Excess solvent was removed under vacuum and the residue was treated with water and ethyl acetate. The organic layer was separated and dried ($Na_2SO_4$). Removal of the solvent on the rotary evaporator gave a residue which was chromatographed on silica gel using 30% ethyl acetate/hexane as the eluent to give 1.75 g (96%) of the title compound as an oil. NMR (ppm, $CDCl_3$): 2.28 (3H, s);

4.65 (2H, s); 7.10 (1H, d, J=8 Hz); 7.15 (1 h, s); 7.30 (1 h, d, J=8 Hz).

Preparation of
4-(chloromethyl)-N-cyclohexyl-3-methyl-N-(1-cyclopentyl)benzamide

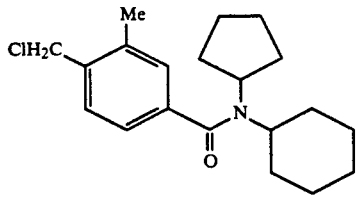

The above described benzyl alcohol XXXV of Scheme K (1.72 g, 0.0054 moles) in 20 mls of thionyl chloride was warmed to 45° C. for 1 hour. Excess thionyl chloride was stripped off on the rotary evaporator. The residue was dissolved in ethyl acetate and washed with dilute aqueous NaHCO3 solution and water. After drying (MgSO4) and removal of solvent, the chloride XXXVI of Scheme K was isolated as a crude oil which weighed 1.63 g (85%). Anal calcd. for $C_{20}H_{28}NOCl$: C, 71.94; H, 8.45; N, 4.19; Cl, 10.62. Found: C, 71.98; H, 8.54; N, 4.18; Cl, 10.45. NMR (ppm, CDCl3): 2.40 (3H, s); 4.40 (2H, s); 7.15 (1 h, d, J=8 Hz); 7.18 (1 h, s); 7.32 (1 h, d, J=8 Hz).

Preparation of
N-cyclohexyl-N-cylcopentyl-4-(5H-imidazo4,5-cl pyridin-5-ylmethyl)-3-methylbenzamide

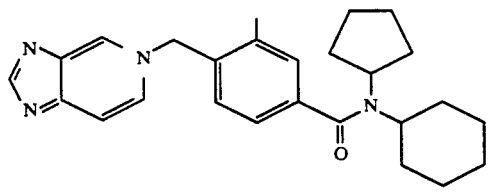

A solution of the above described benzyl chloride XXXVI of Scheme K (500 mg, 0.0015 moles) and imidazopyridine (200 mg) in dry DMF (7mls) was stirred overnight at 25° C. under a nitrogen atmosphere. After warming the reaction mixture to 60° C. for 3 hours to complete the reaction, the solvent was removed in vacuo using the rotary evaporator. The residue was dissolved in 25 mls of methylene chloride, washed with dilute NH4OH (10 mls) and dried (Na2SO4) After removal of the solvent, the residue was chromatographed on silica gel (20 g) using 90/10/1 CH2lC2:MeOH:NH4OH to yield 220 mg (23%) of the title compound. The resulting product has the following properties: m.p. 189-191° C. Anal. calcd. for $C_{26}H_{32}N_4O \cdot H_2O$: C, 71.86; H, 7.89; N, 12.89. Found: C, 72.23; H, 7.72; N, 12.47. NMR (ppm, CDC13): 2.30 (3H, s); 5.50 (2H, s); 6.95 (1 h, s, J=8 Hz); 7.18 (1 h, d, J=8 Hz); 7.22 (1 h, d); 7.22 (1 h, s); 7.70 (1 h, d, J=6 Hz); 7.85 (1 h, d, J=6 Hz); 8.55 (1 h, s); 8.65 (1 h, s).

EXAMPLE 67

Preparation of
N-Cyclopentyl-N-(3,5-dimethylcyclohexyl)-2-methoxy-4-[(7-methoxy-4-methyl-5H-imidazo[4,-5-c]pyridin-5-yl) methyl]benzamide

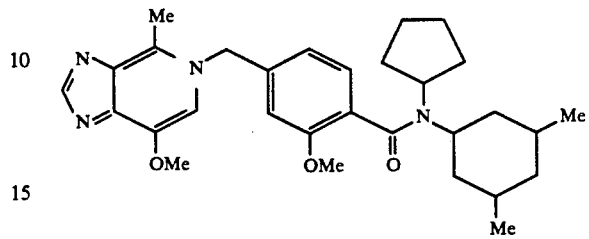

4-Methyl-7-methoxy-imidazo[4,5-c]pyridine was prepared according to Scheme E

Synthesis of 1-[[(2-trimethylsilyl) ethoxy]methyl]-1 h-imidazo[4,5-c]pyridine (Compound V, Scheme E) and 3-[[2(trimethylsilyl) ethoxy]methyl]-3H-imidazo[4,5-c]pyridine (Compound VI, Scheme E)

To a cold solution of imidazo[4,5-c]pyridine (16.5 g, 0.14 mol) in dimethylformamide (150 ml) at 0-5° C., sodium hydride (8.3 g, 60% dipersion in mineral oil, 0.21 mol) was added in 5 portions over 30 min. After stirring 0-5° C. for 15 min, the reaction mixture was allowed to warm to room temperature (approx. 22° C.) and stirred for 3 hr. After recooling to −10° C., 2-(trimethylsilyl)ethoxymethyl chloride (30 ml, 0.17 mol) in dimethylformamide (50 ml) was added over 15-20 min. The cold bath was removed and the reaction mixture was stirred for additional 4 hr. The reaction was carefully quenched with drops of 1N HCl and the solvent removed under reduced pressure. The crude product was resuspended in methylene chloride and washed with aqueous potassium carbonate, water and brine. After drying (MgSO4), filteration and concentration, the crude (37 g) was chromatographed (silica gel, methylene chloride/i-propanol/ammonium hydroxide 90/10/1) to give Compound VI (7.1 g, 20%) and Compound V (12.5 g, 36%).

Compound V. Anal calcd. for $C_{12}H_{19}N_3OSi \cdot 0.2H_2O$: C, 56.97; H, 7.73; N, 16.61. Found: C, 57.01; H, 7.62; N, 16.47. 1H NMR (CDCl3) 9.2 (d, J=2 Hz, 1H), 8.53 (d, J=7 Hz, 1H), 8.10 (s, 1H), 7.53 (dd, J=7, 2 Hz, 1H), 5.6 (s, 2H), 3.56 (t, J=8 Hz, 2H), 0.95 (t, J=8 Hz, 2H), 0.4 (s, 9H).

Compound VI. Anal. calcd. for $C_{12}H_{19}N_3OSi \cdot 0.75 H_2O$: C, 54.82; H, 7.86; N, 15.98. Found: C, 54.75; H, 7.99; N, 15.87. 1H NMR (CDCl3) 9.05 (broad s, 1H), 8.55 (d, CHN J=7 Hz, 1H), 8.14 (s, 1H), 7.78 (dd, J=7, 2 Hz, 1 h), 5.67 (s, 2H), 3.58 (t, J=8Hz, 2H), 0.98 (t, J=8 Hz, 2H), 0.0 (s, 9H).

Synthesis of phenyl
1,4-dihydro-4-methyl-1-[[2-(trimethylsilyl)ethoxy]methyl]-5H-imidazo[4,5-c]pyridine-5-carboxylate
(Compound VII, Scheme E)

To a cold solution (−20° C., CCl4-dry ice bath) of V (1 g, 4 mmol) in THF (20 ml), methyl magnesium bromide (1.47 ml, 3M solution in ether, 4.4 mmol) was added. A solution of phenyl chloroformate (0.52 ml, 4 mmol) in THF (10 ml) was added over 15-20 min. After stirring at −20° C. for 30 min, the cold bath was removed and the reaction stirred for 30 min. The reaction was quenched with water and extracted with ethyl acetate. The organic layer was washed with aqueous sodium bicarbonate, water and brine. After drying (MgSO₄), the solvent was removed and the crude product (1.55 g) chromatographed (silica gel, ethyl acetate-/acetone 98/2) to give Compound VII (1.42 g, 93%) as a colorless liquid. Anal calcd. for $C_{20}H_{27}N_3O_3Si$: C, 62.31; H, 7.06; N, 10.90 Found: C, 62.02; H, 7.08; N, 10.85.

Synthesis of phenyl 1,4,6,7-tetrahydro-6-hydroxy-4-methyl-7-oxo-1-[[2-(trimethylsilyl)ethoxy]methyl]-5H-imidazo[4,5-c]pyridine-5-carboxylate (Compound X, Scheme E) and phenyl 1,4,6,7-tetrahydro-6,7-dihydroxy-4-methyl-1-[[2-(trimethylsilyl)ethoxy]methyl]-5H-imidazo[4,5-c]pyridine-5-carboxylate (Compound XI, Scheme E)

To a clear solution of VII (17 7 g, 46 mmol) in acetone/water (360 ml, 5/1), 4-methylmorpholine N-oxide (6.96 g, 51.5 mmol) and osmium tetroxide (60 ml, 2.5 wt % solution in tert-butanol, 5.9 mmol) were added. After stirring the mixture at room temperature for 48 hr, an aqueous solution of sodium hydrosulfite (200 ml, 1 wt % solution in water) was added. The reaction mixture was stirred for 30 min and filtered. The residue was washed with acetone (300 ml) and the combined organic fractions were concentrated to remove part of the solvent. The mixture was diluted with ethyl acetate (1.2 litre) and washed with brine. The organic layer was dried over MgSO₄ and concentrated. The residue was dissolved in methanol (200 ml) and adsorbed over silica gel. The crude material adsorbed over silica gel was chromatographed (hexane/ethyl acetate 6/4) to give Compound X (8.6 g, 45%) and Compound XI (1.8 g, 9%) respectively.

Compound X. ¹H NMR (CDCl₃, ppm) 8.00 (s, 1H), 7.38 (t, J=7.5 Hz, 2H), 6.42, 6.19 (broad s, 1 h), 6.15 (broad s, 1 h), 5.72 (d, J=11 Hz, 1H), 5.58 (d, J=11 Hz, 1H), 5.53, 5.46 (broad m, 1H), 3.63 (t, J=8.5 Hz, 2H), 1.86, 1.80 (broad m, 3H), 0.94 (t, J=8.5 Hz, 2H), 0.0 (s, 9H).

Compound XI. ¹H NMR (CDCl₃, ppm) 7.62 (s, 1H), 7.37 (t, J=7.5 Hz, 2H), 7.23 (t, J=7.5 Hz, 1H), 7.10 (d, J=7.5 Hz, 2H), 6.27 (d, J=4 Hz, 1H), 5.69 (d, J=10 Hz, 1H), 5.22 (d, J=10 Hz, 1H), 5.17 (broad q, J=6 Hz, 1 h), 5.02 (d, J=4 Hz, 1H), 3.56 (t, J=8 Hz, 2H), 1.78 (d, J=6 Hz, 3H), 0.93 (m, 2H), 0.03 (s, 9H).

Synthesis of phenyl 6-(acetyloxy)-1,4,6,7-tetrahydro-4-methyl-7-oxo-1[[2-(trimethylsilyl)ethoxy]methyl]-5H-imidazo[4,5-c]pyridine-5-carboxylate (Compound XII, Scheme E)

To a clear solution of X (5.2 g, 12.47 mmol) in methylene chloride (100 ml), triethylamine (8.6 ml, 61.5 mmol)), 4-dimethylaminopyridine (220 mg, 1.8 mmol) and acetic anhydride (3.5 ml, 37 mmol) were added. The reaction mixture was stirred at room temperature for 18 hr. After diluting with methylene chloride (400 ml), the reaction mixture was washed with aqueous sodium bicarbonate and brine, dried (MgSO₄) and filtered. The crude product obtained after concentration was chromatographed (silica gel, hexane/ethyl acetate 1/1) to give Compound XII (5.1 g, 89%). ¹H NMR (CDCl₃, ppm) 7.94 (s, 1H), 7.39 (m, 3H), 7.21 (m, 3H), 5.71 (d, J=11 Hz, 1H), 5.63 (d, J=11 Hz, 1H), 5.55, 5.44 (broad m, 1H), 3.66 (t, J=8 Hz, 2H), 2.11 (broad s, 3H), 1.79, 1.72 (broad m, 3H), 0.96 (t, J=8 Hz, 2H), 0.0 (s, 9H).

Synthesis of phenyl 1,4,6,7-tetrahydro-4-methyl-7-oxo-1-[[2-(trimethylsilyl)ethoxy]methyl]-5H-imidazo[4,5-c]pyridine-5-carboxylate of (Compound XIII, Scheme E (Using SmI₂))

To a cold solution of samarium iodide (400 ml, 0.1 M solution in THF, 40 mmol) at −70° C., a solution of XII (5 g, 10.9 mmol) in methanol/THF (100ml, 2/1) was added in dropwise fashion. The reaction was stirred at −70° C. for 20 min and then allowed to warm to room temperature. At around 0° C., the blue color of reaction fades and turns to pale yellow. The reaction was stirred at room temperature for 1 hr and then poured into saturated aqueous potassium carbonate (600 ml).

The reaction mixture was extracted with ethyl acetate (2×800 ml) and washed with brine. After drying (MgSO₄) and concentration, the crude mixture (6.4 g) was chromatographed (silica gel, hexane/ethyl acetate 1/1) to give pure Compound XIII (2.98 g, 68%). Anal calcd. for $C_{20}H_{27}N_3O_4Si]0.8$ H₂O: C, 57.75; H,6.93; N, 10.10 Found C, 57.74; H,6.73; N, 9.94.

Synthesis of Phenyl 1,4,6,7-tetrahydro-4-methyl-7-oxo-1-[[2-(trimethylsilyl)ethoxy]methyl]-5H-imidazo[4,5-c]pyridine-5-carboxylate (Compound XIII, Scheme E (Using CrCl₂))

Synthesis of CrCl₂: To a suspension of zinc dust (1 g) and mercuric chloride (80 mg) in water (1 ml), conc. HCl (0.1 ml) was added. After stirring under argon for 10 min., the mixture was allowed to stand and the supernatent liquid was decanted. To this, a solution of CrCl₃ (1.2 g) in water (1.5 ml) containing conc. HCl (2.5 ml) was added. The mixture Was stirred for 10 min when the greenish Cr+³ salt turned to bluish Cr+² solution. This was stored under argon and used in the deoxygenation reaction as shown below.

To a solution of Compound XII of Scheme E (330 mg, 0.72 mmol) in acetone (4 ml), a freshly generated CrCl₂ solution (1 ml) was injected in dropwise. The reaction was followed by TLC and after the disappearance of starting material (approx. 30 min), the reaction mixture was concentrated to remove acetone. The residue was redissolved in chloroform and washed with brine. The organic layer was separated, concentrated and the crude chromatographed (silica gel, ethyl acetate/acetonitrile 100/1.5) to give Compound XIII (199 mg, 69%) and Compound X (39 mg, 13%) with analytical and spectral properties identical to the respective products obtained in the above examples.

Synthesis of 4-methyl-1-[[2-(trimethylsilyl)ethoxy]methyl]-1 h-imidazo [4,5-c]pyridin-7-ol (Compound XIV, Scheme E)

A clear solution of Compound XIII (0.4 g, 1 mmol) in EtOH/H₂O/NaOH (30/30/2) was heated at 75–80° C. for 18 hr. After cooling, the reaction mixture was neutralized with 6N HCl and part of the solvent was removed under reduced pressure. The crude mixture was repeatedly extracted with methylene chloride and the organic layer was washed with aqueous sodium bicarbonate and brine. The organic layer was dried (MgSO₄) and concentrated. The residue (370 mg) was chromatographed (silica gel, methylene chloride/methanol/ammonium hydroxide 90/10/1) to give Compound XIV (47 mg, 17%); $^1$H NMR (CD$_3$OD, ppm) 8.35 (s, 1H), 7.65 (s, 1 h), 5.87 (s, 2H), 3.65 (t, J=8 Hz, 2H), 2.68 (s, 3H), 0.87 (t, J=8 Hz, 2H), −0.07 (s, 9H).

Synthesis of 7-methoxy-4-methyl-1-[[2-(trimethylsilyl)ethoxy]methyl]-1 h-imidazo [4,5-c]pyridine (Compound XV, Scheme E)

To a clear solution of Compound XIV (51 mg, 0.18 mmol) in DMF (5 ml), sodium hydride (17 mg, 60% dispersion in mineral oil, 0.22 mmol) was added and the mixture was stirred for 15 min. Iodomethane (14 μl) was added and the mixture was stirred under argon for 18 hr. The reaction was neutralized with acetic acid and the solvent was removed under reduced pressure at <45° C. The residue was diluted with methylene chloride and washed with aqueous sodium bicarbonate, water and brine. After concentration of the organic layer, the crude (65 mg) was chromatographed (silica gel, methylene chloride/methanol/ammonium hydroxide 95/5/0.5) to give Compound XV (27 mg, 51%); $^1$H NMR (CDCl$_3$, ppm) 8.02 (s, 1 h), 8.0 (s, 1 h), 5.78 (s, 2H), 4.08 (s, 3H), 3.62 (t, J=8 Hz, 2H), 2.87 (s, 3H), 0.97 (t, J=8 Hz, 2H), 0.0 (s, 9H).

Synthesis of 7-methoxy-4-methyl-1 h-imidazo[4,5-c]pyridine (Compound XVI, Scheme E)

A solution of Compound XV (25 mg, 0.085 mmol) in trifluoroacetic acid (2 ml) was heated at 50° C. for 6 hr. The solvent was removed and the crude chromatographed on silica gel using methylene chloride/methanol/ammonium hydroxide (90/10/1) to give Compound XVI (13 mg, 93%). $^1$H NMR (CD$_3$OD, ppm) 8.28 (s, 1H), 7.84 (s, 1 h), 4.06 (s, 3H), 2.74 (s, 3H).

B. Preparation of Halomethyl Benzamides

The halomethyl benzamides were prepared according to Scheme L.

Methyl 2-methoxy-4-methylbenzoate:

Methyl iodide (123 mL, 1.95 mole) was added to a stirred suspension of potassium carbonate (360.0 g, 2.60 mole) in a solution of 2-hydroxy-4-methylbenzoic acid (100.0 g, 0.651 mole) in dimethylformamide (1500 mL) at room temperature. After stirring overnight, the reaction mixture was poured onto ice water (1000 mL) and the aqueous mixture extracted several times with ethyl acetate. The organic layers were combined, dried (Na$_2$SO$_4$), and stripped in vacuo to give a brown oil. After passage over silica gel using 20% ethyl acetate/hexane as the eluent, there was obtained 116.7 g of the title compound as an oil which was a single spot on thin layer chromatography (R$_f$ 0.35, 20% ethyl acetate/hexane). NMR (CDCl$_3$, 300 MHz, ppm): 2.4 (s, 3H); 3.87 (s, 3H); 3.9 (s, 3H); 6.78 (s, 1H); 6.8 (d, 1 =J Hz, 1 h); 7.72 (d, J=7 Hz, 1H).

Methyl 4-bromomethyl-2-methoxybenzoate:

A solution of methyl 2-methoxy-4-methyl benzoate (99.0 g, 0.55 mole), N-bromosuccinimide (109.0 g, 0.61 mole) and bisazoisobutyronitrile (50 mg) in carbon tetrachloride (1000 mL) was refluxed under an argon atmosphere while a sun lamp was directed on the flask. After 75 min., the heat lamp was removed and the reaction mixture was allowed to cool. During the reaction, the color of the solution had changed from light orange to dark orange to light yellow. After cooling, the reaction mixture was washed three times with 10% sodium bicarbonate, dried (MgSO$_4$) and solvent removed to yield the crude product as an amber oil. After chromatography on silica gel using 20% ethyl acetate/hexane as the eluent, there was obtained 104 g (70%) of the titled product as a crystalline solid, m. pt, 55-56°. NMR (CDCl$_3$, 300 MHz, ppm): 3.88 (s, 3H); 3.92 (s, 3H); 4.45 (s, 2H); 7.0 (s, 1 h); 7.01 (d, J=7.5 Hz, 1H); 7.78 (d, J=7.5 Hz, 1 h).

4-Hydroxymethyl-2-methoxybenzoic acid:

A mixture of methyl 4-bromomethyl-2-methoxybenzoate (25.0 g, 96.5 mmol), potassium hydroxide (10.83 g, 193 mmol) and water (400 mL) was refluxed with stirring for 2 hr. The reaction mixture was cooled, further basified to pH 14, and extracted three times with ethyl ether. The reaction solution was then acidified to pH 1 and extracted several times with ethyl acetate. The ethyl acetate layers were combined, dried (Na$_2$SO$_4$) and evaporated to yield 16.3 g (93%) of the title compound as an off white solid, m. pt 106-111°, whose purity was suitable for use without further purification. Additional purification is effected by recrystallization from ethyl acetate and hexane, m. pt, 112-115°.

NMR (CDCl$_3$/d6-DMSO, 300 MHz, ppm): 4.00 (s, 3H); 4.70 (s, 2H); 7.00 (d, J=7.5 Hz, 1 h); 7.13 (s, 1H); 7.95 (d , J=7.5 Hz, 1H).

4-Chloromethyl-2-methoxybenzoyl Chloride:

A solution of 4-hydroxymethyl-2-methoxybenzoic acid (10.0 g, 54.9 mmol) in thionyl chloride (100 mL) was refluxed for 3 hrs. The excess thionyl chloride was removed in vacuo and the residue azeotroped three times with toluene to give 12 g (100%) of the title product as a yellow solid. This material is used without further purification. NMR (CDCl$_3$, 300 MHz, ppm): 3.95 (s, 3H); 4.60 (s, 2H); 7.03 and 7.05 (2H, overlapping s and d , J for d=7.5 Hz); 8.18 (d , J=7.5 Hz , 1H).

4-Chloromethyl-2-methoxybenzoic acid N-cyclopentyl-N-3,5-dimethylcyclohexyl amide:

A solution of the acid chloride described above (14.6 g, 66.7 mmol) in dry tetrahydrofuran (50 mL) was added dropwise to a cold (0°) stirred solution of N-cyclopentyl-N-3,5-dimethylcyclohexyl amine (16.25 g, 83.2 mmol) and triethylamine (8.51 g, 83.3 mmol) in dry tetrahydrofuran (50 mL). The ice bath was removed and the reaction mixture was stirred at room temperature for 2 hrs. The reaction mixture was filtered and the filtrate concentrated in vacuo to give a brown glass. The glass was chromatographed on silica gel using 20% ethyl acetate/hexane as the eluent and the isolated product was recrystallized from hexane to give 13.6 g (54%) of the title compound as an off white solid, m. pt. 143-144°. NMR (CDCl$_3$, 300 MHz, ppm): 0.45 (q, J=12 Hz, 1H); 0.73 (q, J=12 Hz, 1H); 0.8-1.80 (m, 16H); 2.0 (m, 2H); 2.32 (m, 2H); 2.98 (tt , J=12, 2 Hz , 0.5H); 3.24 (tt, J=12, 2 HZ, 0.5 H); 3.58 (p, J=9 Hz, 0.5 H); 3.78 (p, J=9Hz, 0.5 H); 3.81 (s, 3H); 4.57 (s, 2H); 6.90 (s , 1 h); 6.95 (d , J=8 Hz , 1H); 7.1 ( 1H, 2 overlapping d, J=8 Hz).

4-Chloromethyl-2-methoxybenzoic acid N-cyclobutyl-N-cyclohexyl amide:

A solution of the acid chloride described above (6.0 g, 27.4 mmol) in dry tetrahydrofuran (15 mL) was added dropwise to a cold (0°) stirred solution of N-cyclobutyl-N-cyclohexyl amine (5.25 g, 34.2 mmol) and triethylamine (4.77 mL g, 34.2 mmol) in dry tetrahydrofuran (15 mL). The ice bath was removed and the reaction mixture was stirred at room temperature for 2 hrs. The reaction mixture was filtered and the filtrate concentrated in vacuo to give a brown glass. The glass was chromatographed on silica gel using 20% ethyl acetate/hexane as the eluent and the isolated product was recrystallized from hexane to give 4.98 g (54%) of the title compound as an off white solid, m. pt, 92–93°. NMR (CDCl₃, 300 MHz, ppm): 0.90–2.20 (m, 16H); 2.55 (m, 1 h); 3.05–3.45 (m, 1H); 3.89 (m, 1H); 3.82 (s, 3H); 4.59 (s, 2H); 6.90 (s, 1H); 6.95 (d, J=8 Hz, 1H); 7.12 (d, J=8 Hz, 1 h)

cis, cis-3,5-Dimethylcyclohexyl amine (Scheme M):

3,5-Dimethylaniline (45.1 g, 0.37 mole) was hydrogenated in methanol at 1000 psi and 120° for 15 hrs using 5% ruthenium on carbon as catalyst. The reaction mixture was concentrated in vacuo and the residue vacuum distilled at 80° (30 mm Hg) to give 32 g (68%) of the product as a clear, colorless oil. NMR (CDCl₃, 300 MHz , ppm): 0.50 (q , J=10 Hz , 1H); 0.90 (d, J=5 Hz, 6H); 1.20 (s, broad, 1H); 1.40–1.65 (m, 3H); 1.80 (m, 2H) ,2.65 (tt , J=5, 10 Hz , 1H).

N-cis, cis-3,5-Dimethylcyclohexyl-N-cyclopentyl amine (Scheme M):

A solution of cis, cis-3,5-dimethylcyclohexylamine (68 g, 0.55 mol) and cyclopentanone (46.27 g, 0.55 mole) in ethanol was hydrogenated at 60 psi and room temperature for 26 hrs. using 5% palladium on carbon as the catalyst. The reaction mixture was concentrated in vacuo and the residue vacuum distilled at 104–112° (2 mm Hg) to give 90.47 g (84%) of the title product as a clear, colorless oil. NMR (CDCl3, 300 MHz, ppm): 0.52 (q, J=17 Hz , 1H); 0.65 (q , J=17 Hz, 1H); 0.90 (d, J =6 Hz , 6H) 1.2–1.3 (m , 1 h); 1.35–1.75 (m, 11H); 1.8–1.9 (m, 2H); 2.52 (tt, 1=11, 2.5 Hz, 1H); 3.21 (pentet, J=7 Hz, 1H).

C. Preparation of N-Cyclopentyl-N-(3,5-dimethylcyclohexyl)-2-methoxy-4-[(7-methoxy-4-methyl-5H-imidazo[4,-5-c]pyridin-5-yl) methyl]benzamide To a stirred solution of compound XVI of Scheme E (14 mg, 0.085 mmol) in N,N-dimethylformamide (5 mL), 4-bromomethyl-2-methoxy-N-cyclopentyl, N-3,5-dimethylcyclohexyl benzamide (40 mg, 0.09 mmol) was added. After stirring at room temperature for 48 hr, the reaction mixture was neutralized with drops of dilute ammonium hydroxide. The solvent was removed under reduced pressure at <45° C. and the residue (56 mg) was chromatographed (silica gel , CH2Cl2/MeOH/NH₄OH 90/10/1) to give the title product (12 mg, 28%); Anal calcd. for C₃₀H₄₀N₄O₃·H₂O:C, 68.94; H, 8.10; N, 10.72 Found C, 68.69; H, 7.76; N, 10.41.

EXAMPLE 68

Preparation of N-cylcopentyl-N-(3,5-dimethylcyclohexyl)-2-methoxy-4-[(4-methyl-5H-imidazo[4,5-c1pyridin-5-yl)methyl benzamide

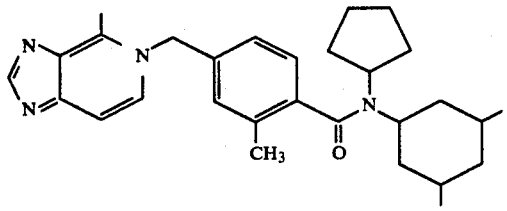

A. 4-Nitro-2-picoline-N-oxide (XXVII, Scheme C):

To a stirred solution of 2-picoline-N-oxide (50 g, 0.46 mole) in con. sulfuric acid (175 mL) at 5° was added fuming nitric acid (138 mL) over 30 min. while maintaining the temperature <10°. After completion of addition, the vessel was heated to 100° with good stirring for 2 hrs. The reaction mixture was cooled to room temperature, poured onto ice and basified to pH 9 with potassium carbonate. The reaction mixture was extracted three times with chloroform. The combined organic layers were washed once with water and dried (Na₂SO₄). The solution was filtered and the filtrate concentrated in vacuo to give 64 g (90%) of the crude product (XXVII). An analytical sample was prepared by recrystallization from acetone, m. pt. 158–160° [lit. m. pt. 159–161°; A. R. Katritzky et al, J. Chem. Soc., 1769 (1957)]. Recrystallization may also be carried out using toluene/hexane.

Anal. calcd for C₆H₆N₂O₃:C, 46.76; H, 3.92; N, 18.18. Found: C, 46.81; H, 3.86; N, 18.01.

4-Amino-2-picoline (XXVIII, Scheme C):

4-Nitro-2-picoline-N-oxide (31.1 g, 0.202 mole) was hydrogenated in 1:1 methanol:tetrahydrofuran (500 mL) at 5 psi at room temperature for 130 min. using Raney Nickel as the catalyst. The reaction mixture was filtered and stripped in vacuo. The residue was recrystallized from toluene to give 15 g (70%) of the title compound XXVIII, m. pt. 90–91° [See A. R. Katritzky et al, J . Chem. Soc., 1769 (1957)].

Anal. calcd for C₆H₈N₂: C, 66.64; H, 7.46; N, 25.90. Found: C, 66.77; H, 7.52; N, 25.66.

4-Nitramino-2-picoline (XXIX, Scheme C):

4-Amino-2-picoline (25 g, 0.23 mole) was added in portions to stirred con. sulfuric acid (120 mL) at <40° C. under an argon atmosphere. The resulting solution was cooled to 0° and fuming nitric acid was added slowly over 45 min. while maintaining the temperature at <4°. After the completion of addition, the reaction mixture was stirred at 0° for 30 min. and then poured onto ice (ca. 250 g). The flask containing the ice was externally cooled with dry ice-acetone such that the internal temperature was maintained at <20°. The resulting aqueous solution was neutralized to pH 8–9 using con. ammonium hydroxide, maintaining the temperature at <25°. The red precipitate that formed was filtered and air dried. This solid was dissolved in water by warming on the steam bath and adjusting the pH to 7.5–8.0 if necessary. Upon cooling, the purified product crystallized out. Two crops of 15.0 g and 3.0 g were obtained for a total yield of 51% of the title compound XXIX. M. pt. 191–194° [See B. Brekiesz-Lewandowska, Z. Talik, Rocz. Chem., 44 ( I ), 69–75 (1970); Chem. Abstracts , 73, 45415 n].

4-Amino-3-nitro-2-picoline (XXX, Scheme C):

The above nitramine XXIX (20 g, 0.13 mole) was added in portions to con. sulfuric acid (200 mL) maintained at 5° and the solution was warmed to 60° under a nitrogen atmosphere for 4 hrs. The reaction mixture was cooled, poured onto ice, neutralized to pH 7.5–8.0 and extracted twice with chloroform. The combined organic layers were washed once with water and dried (Na₂SO₄). The drying agent was filtered and the filtrate concentrated in vacuo to give 12 g of crude product. Recrystallization of this material from ethyl acetate gave 5.5 g of title compound XXX, m. pt. 171–174°.

Anal. calcd. for C₆H₇N₃O₂: C, 47.06; H, 4.61; N, 27.44. Found: C, 47.10; H , 4.65; N, 27.14.

3,4-Diamino-2-picoline (XXXI, Scheme C):

4-Amino-3-nitro-2-picoline (5.5 g, 0.036 mole) was hydrogenated in methanol (250 mL) at 5 psi and 25° for 1.25 hr using Raney Nickel as catalyst. The catalyst was filtered, the filtrate stripped in vacuo and the residue triturated with cyclohexane to give a solid. The solid was filtered and air dried to give 4.0 g (88%) of the title compound, m. pt. 170–171°.

Anal. calcd for C<sub>6</sub>H<sub>9</sub>N<sub>3</sub>: C, 58.52; H, 7.37; N, 34.12. Found: C, 58.82; H, 7.31; N, 34.42.

4-Methyl-1(H)-imidazo[4,5-c]pyridine (Scheme C):

A solution of 3,4-diamino-2-picoline (4.0 g, 0.032 mole) and p-toluenesulfonic acid (100 mg) in triethylorthoformate (40 mL) was heated at 100° under a nitrogen atmosphere until the reaction was complete (26 hr). The reaction mixture was cooled and the solvent removed at reduced pressure with heating (50°). The residue was triturated with ethyl acetate until solid, filtered and recrystallized from ethanol to give 3.5 g (91%) of the title compound, m. pt. 225–227°.

Anal. calcd for $C_7H_7N_3$:C, 63.14; H, 5.30; N, 31.56. Found: C, 62.70; H, 5.30; N, 31.10.

B. Preparation of N-cyclopentyl-N-(3,5-dimethylcyclohexyl)-2-methoxy-4-[(4-methyl-5H-imidazo[4,5-c]pyridin-5-yl)methyl]-benzamide A solution of 4-methyl-1(H)-imidazo[4,5-c]pyridine (1.4 g, 0.011 mole) and 4-chloromethyl-2-methoxy benzoic acid N-cyclopentyl-N-3,5-dimethylcyclohexyl amide (3.88 g, 0.010 mole) in dimethylformamide (40 mL) was heated at 60° with stirring under a nitrogen atmosphere for 26 hrs. The reaction solvent was removed in vacuo using an oil pump with heating (40°) and the residue chromatographed on silica gel using MeOH:CH<sub>2</sub>Cl<sub>2</sub>:0.5N NH<sub>4</sub>OH (7:93:1) to give 1.8 g of the title compound as an oil. The product crystallized when treated with 30% ethyl acetate/hexane and was filtered to give 1.53 g (37%) of pure product, m. pt. 232–234° (capillary); 233° (DSC). <sup>1</sup>H NMR (CDCl<sub>3</sub>, ppm): 8.55 (s, 1H), 7.75 (d, J=6 Hz, 1H), 7.70 (d, J=6 Hz, 1H), 7.10 (s, 1H), 6.50 (d, J=10 Hz, 1 h); 6.45 (d, J=10 Hz, 1 h); 5.50 (s, 2H); 3.70 (s, 3H); 2.95 (s, 3H).

Anal. calcd for C<sub>29</sub>N<sub>38</sub>N<sub>4</sub>O<sub>2</sub>: C, 73.39; H, 8.07; N, 11.80. Found: C, 73.27; H, 8.32; N, 11.78.

EXAMPLE 69

Preparation of N-cyclohexyl-3-methoxy-N-(1-methylethyl)-4-[(4-methyl-5H-imidazo[4,5-c1pyridin-5-yl)methyl]benzamide

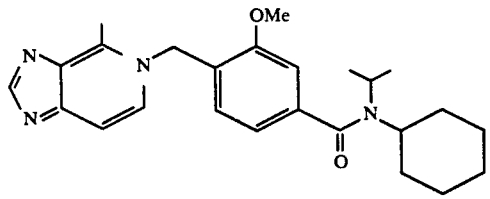

A. Preparation of 4-methyl-1H-imidazo[4,5-c]pyridine

Synthesis of 1-[[(2-trimethylsilyl)ethoxy]methyl]-4-methyl-1H-imidazo[4,5-c]pyridine (Compound VIII, Scheme B)

A clear solution of Compound VII (0.9 g, 2.33 mmol) (described in Schemes B and E) in EtOH/H<sub>2</sub>O/NaOH (30/30/2) was heated at 80° C. for 20 hr. After cooling, the reaction mixture was brought to pH 8 by adding 3N HCl and part of the solvent was removed under reduced pressure. The crude mixture was repeatedly extracted with methylene chloride (3×200 ml), dried (MgSO<sub>4</sub>) and concentrated. The residue (0.82 g) was redissolved in ethanol (75 ml) and refluxed under air for 20 hr. After removal of the solvent, the crude was chromatographed (silica gel, methylene chloride/methanol 94/6) to give Compound VIII (171 mg, 28%), <sup>1</sup>H NMR (CDCl<sub>3</sub>, ppm) 8.4 (d, J=7Hz, 1H), 8.07 (s, 1H), 7.38 (d, J=7 Hz, 1H), 5.58 (s, 2H), 3.56 (t, J=8 Hz, 2H), 2.95 (s, 3H), 0.96 (t, J=8 Hz, 2H), 0.0 (s, 9H).

Synthesis of 4-methyl-1 h-imidazo[4,5-c]pyridine (Compound IX, Scheme B)

A solution of Compound VIII (750 mg, 2.85 mmol) in trifluoroacetic acid (10 ml) was heated at 50° C. for 18 hr. The solvent was removed, diluted with methanol and neutralized with cold dilute ammonium hydroxide. The solvents were removed under reduced pressure and the crude chromatographed on silica gel using methylene chloride/methanol/ammonium hydroxide (90/10/1) to give Compound IX (350 mg, 92%). <sup>1</sup>H NMR (CD<sub>3</sub>OD, ppm) 8.48 (s, 1H), 8.18 (d, J=7Hz, 1H), 7.47 (d, J=7 Hz, 1H), 2.82 (s, 3H).

B. Preparation of N-cyclohexyl-3-methoxy-N-(1-methylethyl)-4-[(4-methyl-5H-imidazo[4,5-c]pyridin-5-yl)methyl]benzamide To a stirred solution of 4-methyl-1 h-imidazo [4,5-c]pyridine Compound IX (Scheme B) (200 mg, 1.5 mmol) in N,N-dimethylacetamide (25 mL), 4-bromomethyl-3- methoxy-N-isopropyl, N-cyclohexyl benzamide (547 mg, 1.5 mmol) was added. After stirring at room temperature for 60 hr, the solvent was removed under reduced pressure at <45° C. and the residue (800 mg) was chromatographed (silica gel, CH<sub>2</sub>Cl<sub>2</sub>/MeOH/NH<sub>4</sub>OH 90/10/1) to give the title compound (220 mg, 35%), mp 185–87° C. (shrinks) and melts at 227–29° C.; Anal calcd. for C<sub>25</sub>H<sub>32</sub>N<sub>4</sub>O<sub>2</sub>·0.3 H<sub>2</sub>O: C, 70.49; H, 7.71; N, 13.15. Found: C, 70.41; H, 7.82; N, 13.00. <sup>1</sup>H NMR (CDCl<sub>3</sub>, ppm) 8.53 (S, 1H), 7.68 (d, J=7Hz, 1H), 7.63 (d, J=7 Hz, 1H), 6.93 (d, J=2Hz, 1H), 6.78 (dd, J=8, 2 Hz, 1H), 6.56 (d, J=8 Hz, 1H), 5.47 (s, 2H), 3.87 (s, 3H), 3.2–3.7 (complex band, 2H), 2.97 (s, 3H), 0.9–1.9 (complex band, 16H).

EXAMPLE 70

Preparation of N-cyclobutyl-N-cyclohexyl-2-methoxy-4-[(4-methyl-5H-imidazo[4,5-c]pyridin-5-yl)methylbenzamide

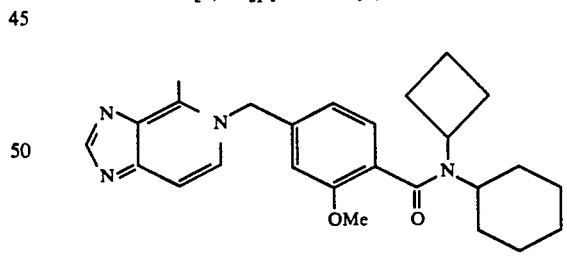

A solution of 4-methyl-1 h-imidazo[4,5-c]pyridine (Compound IX, Scheme B) (400 mg, 0.003 mole) and 4-chloromethyl-2-methoxybenzoic acid N-cyclobutyl-N-cyclohexyl amide (1.0 g, 0.003 mole) in dimethylformamide (5 mL) was stirred at 60° for 16 hr under an argon atmosphere. The reaction solvent was removed in vacuo and the residue chromatographed on silica gel using 93:7:0.5 CH<sub>2</sub>Cl<sub>2</sub>: MeOH:NH<sub>4</sub>OH as the eluent to give the title compound. After recrystallization from ethyl acetate, there was obtained 250 mg of pure material, m. pt. 201–203°.

<sup>1</sup>H NMR(CD<sub>3</sub>OD, 300 MHz, ppm):8.37(s, 1H); 8.22(d, J=6Hz, 1H); 7.75 (d, J=6Hz,1H); 7.13 (d, J=10

Hz, 1H); 6.95 (d, J=10Hz, 1H); 6.60 (s, 1H); 5.81 (s, 2H); 3.75 (s, 3H); 2.95 (s, 3H).

Anal calcd for $C_{26}H_{32}N_4O_2 \cdot 0.25\ H_2O$: C, 71.45; H, 7.50; N, 12.82. Found: C, 70.98; H, 7.52; N, 12.74

EXAMPLE 71

Preparation of N-cyclohexyl-4-[4-(1,1-dimethylethyl)-5H-imidazo[4,5-clpyridin-5-yl)methyl]-3-methoxy-N-(1-methylethyl)benzamide

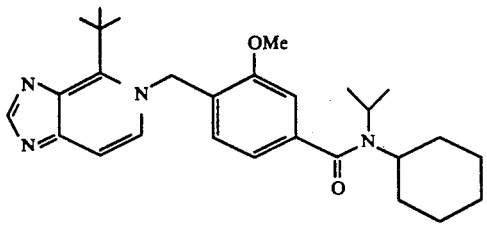

To a stirred solution of 4-tert-butylimidazopyridine (60 mg, 0.34 mmol) in N,N-dimethylformamide (5 mL), 4-bromomethyl-3-methoxy-N-isopropyl, N-cyclohexyl benzamide (150 mg, 0.4 mmol) was added. After stirring at room temperature for 48 hr, the solvent was removed under reduced pressure and the residue was chromatographed (silica gel, $CH_2Cl_2$/MeOH/$NH_4OH$ 90/10/1) to give the title compound (20 mg, 33%), Anal calcd. for $C_{28}H_{38}N_4O_2 \cdot 0.75\ H_2O$: C, 70.63; H, 8.36; N, 11.77 Found: C, 70.77; H, 8.41; N, 10.47. $^1H$ NMR (CDCl$_3$, ppm) 8.33 (d, J=7 Hz, 1 h), 8.0 (s, 1 h), 7.23 (d, J=7 Hz, 1H), 7.05 (d, J=8Hz, 1H), 6.88 (d, J=2 Hz, 1H), 6.83 (dd, J=8, 2 Hz, 1H), 5.31 (s, 2H), 3.87 (s, 3H), 3.2–3.7 (complex band, 2H), 1.64 (s, 9H), 0.9–1.9 (complex band, 16H).

EXAMPLE 72

PAF-induced platelet aggregation and secretion: Washed, [$^3H$]serotonin-labeled rabbit platelets were prepared as previously described in COX, C. P., J. LINDEN and S. I. SAID: VIP elevates platelet cyclic AMP (CAMP) levels and inhibits in vitro platelet activation induced by platelet- activating factor (PAF). Peptides 5:25–28, 1984, and maintained in an atmosphere of 5% $CO_2$ at 37° C. until used in the bioassay. Aliquots of platelets (2.5–10$^8$/ml) were incubated with either an antagonist of PAF or the appropriate vehicle for 60 sec prior to the addition of PAF (0.2 nM to 0.2 mM). Aggregation was continuously monitored on a strip-chart recorder and recorded as the height of the tracing at 60 sec after the the addition of PAF. Secretion of [$^3H$] serotonin was measured in a sample of the platelet suspension removed at 60 sec after the addition of PAF. The percent inhibition of aggregation and secretion was calculated by comparing antagonist-treated platelets with the appropriate vehicle-treated control platelets. Each combination of antagonist and PAF was repeated 12–15 times, using several different platelet preparations. IC$_{50}$ values were determined by inspection of the dose-response curves.

EXAMPLE 73

Inhibition of $^3H$-PAF Binding to Human Platelet Membrane Receptors

Receptor Preparation: Ten units of in-dated human packed platelets, each containing 45–65 ml platelet rich-plasma, were purchased from a commercial blood bank. Disposable plasticware was used throughout for receptor preparation. The units were pooled and a 1 ml aliquot was removed for determination of platelet concentration, using a Coulter Counter. The remaining platelet rich plasma was dispensed into 50 ml conical tubes and centrifuged at room temperature for 15 minutes at 3000 RPM (2300×g). Plasma was decanted and the platelets were resuspended in 35 ml of buffer (10 mM Trizma 7.0, 2 mM EDTA (dipotassium salt), and 150 mM KCl) and transferred to fresh tubes, which were centrifuged again as above. The platelets were washed 3 times, avoiding contaminating erythrocytes at the bottom of the pellets. Pellets were consolidated at each step, and by the last wash with EDTA/KCl buffer, most of the erythrocytes were in 1 tube. The pellets were resuspended in buffer containing 10 mM Trizma 7.0 with 10 mM $CaCl_2$. Following centrifugation, the buffer was decanted and the pellets were resuspended in the $CaCl_2$ buffer, avoiding erythrocyte contamination by recovering less than 100% of the platelet pellets. The resuspended platelets were dispensed in 8–10 ml aliquots into Corex tubes and disrupted by three cycles of freezing (dry ice/ethanol) and thawing (24° C.). The tubes were centrifuged at 40,000×g for 20 minutes at 4° C. Supernatants were decanted and each pellet was resuspended in 5–7 ml 10 mM Trizma 7.0. All resuspended pellets were pooled and aliquots of about 1200 ml were dispensed into 1.5 ml microfuge tubes and frozen at −70° C. Protein-content was determined by a fluorescamine protein assay.

Assay Methods: Receptor Characterization—Each receptor preparation was evaluated to determine the number of receptor populations, the number of PAF receptor equivalents/mg protein and the dissociation constant ($K_D$) for PAF binding. This required 2–3 experiments in which the protein concentration was held constant and the $^3H$-PAF ligand concentration was varied from approximately 0.10–2.5 nM and the data was analyzed by Scatchard methodology. Total incubation volume was 250 ml for these procedures and incubations were conducted at 24° C. for 30 minutes. For further experimentation, total incubation volumes are 500 ml. Protein and ligand concentrations were adjusted to give 0.075 nM receptor equivalents in the presence of 0.75 nM $^3H$-PAF. Each receptor preparation was then used to determine the dose-response displacement relationship of unlabeled PAF and the PAF antagonist, triazolam. As long as the KD value and IC$_{50}$ values for PAF and triazolam were consistent with similar data collected from past receptor preparations used in the assay, the new receptor preparation was used for evaluating compounds.

Assay Methods: Routine Assay of Compounds—The Assay Methods: compounds were weighed precisely and solubilized in quantities of DMSO such that a 5 ml aliquot in the incubate would deliver the desired compound concentration. Compounds tested for the first time in this assay were evaluated at a concentration of 50 mM in the incubation medium. All compounds were generally solubilized in DMSO for about 2 hours prior to assay. Triazolam was always included in each screening assay as a compound inhibition control. A standard concentration of 50 mM inhibited $^3H$-PAF binding by approximately 50%. Nonspecific binding control solution was made by drying to completion about 26.2 ml unlabeled PAF under a stream of argon. PAF was resolubilized in 1000 ml DMSO. When delivered in a 5 ml aliquot, the final concentration of 1 mM PAF in the incubate exceeded by 1000-fold the concentration of $^3$H-PAF.

All buffers containing proteins were made at room temperature on the day of assay. Assay buffer was prepared by adding 125 mg human albumin to 25 ml of stock buffer (10 mM Trizma 7.4 with 20 mM CaCl$_2$). Rinse buffer was made by adding 20 grams bovine serum albumin to 1000 ml stock buffer. About 80 ml of rinse buffer was decanted into a small pyrex dish and used to soak 65 Whatman GF/C 2.5 cm glass filters. The remaining rinse buffer was poured into a repipet and placed into an ice bath along with the filters.

Ligand for assay was prepared by adding about 10 ml of stock $^3$H-PAF (DuPont NEN, NET-668) to 14 ml of assay buffer. Since the amount of $^3$H-PAF in the final incubate was to be 0.75 nM, the actual amount of stock $^3$H-PAF to be used had to be determined for each lot of material based upon its specific activity.

Membrane receptors for assay were prepared by thawing the appropriate number of tubes at room temperature and adding membranes to 10 mM Trizma 7.0 containing 10 mM CaCl$_2$. A total volume of 14 ml Was made. The actual amount of membranes needed was determined by the requirement to have 0.075 nM PAF receptor equivalents per assay tube. All materials were kept in motion by rocking on a rocker plate.

First, 5 ml of compound or DMSO was added to each 12×75 mm polypropylene tube, followed by the addition of 95 ml assay buffer. Next, 200 ml $^3$H-PAF was added to each tube and 3 aliquots of $^3$H-PAF taken at different times during the dispensing were placed in scintillation vials. The reaction was initiated by the addition of 200 ml of membranes. All tubes were very briefly vortexed and placed in a 24° C. water bath for about 30 minutes. During this time, Whatman GF/C filters were placed on the filter racks of 5 Millipore vacuum manifolds. The incubations were terminated by first adding 4 ml ice-cold rinse buffer to each incubation tube and then decanting them over the filters under vacuum. Tubes and filters were rinsed twice more. Each filter was placed into a 20 ml scintillation vial to which 20 ml Aquasol (DuPont NEN, NDF 952) was added. All vials were given 2 hours in the dark for photo and chemiluminence to dissipate prior to liquid scintillation counting.

In summary, each incubation tube contained 500 ml total volume of incubate. This consisted of 5 ml drug with DMSO or only DMSO, 95 ml assay buffer, 200 ml $^3$H-PAF (0.75 nM final concentration) and 200 microleters membrane receptors (0.075 nM final concentration). 60 tubes per assay were run and each dose was performed in triplicate. Controls in every assay consisted of 2 diluent (DMSO) "0" controls (2 triplicate determinations placed at different positions within the 60 tube assay), 1 nonspecific binding control, and 1 triazolam drug control. The 16 remaining doses were used to test 16 different compounds at the screening dose of 50 mM, or to run dose-response determinations for a compound. In general, dose-response curves were composed of 4 compound doses designed to inhibit $^3$-PAF binding by 15-85%, with at least 1 dose on each side of the 50% point.

Routine Assay Calculations: Triplicate DPM determinations (corrected for background) within a single compound dose were averaged while all 6 determinations of total binding ("0" dose, DMSO only) were averaged. The amount for nonspecific binding (1 mM PAF) was subtracted from all the dose averages, giving an amount of specific binding in all cases. The percent displacement of $^3$H-PAF or inhibition of binding was calculated by the formula STBo-SBc/STBo×100, where STBo=specific binding of "0" dose controls and SBc=specific binding in the presence of compound. If a compound tested at the initial screening dose of 50 mM inhibited binding by 45% or more, the compound was considered active and was tested in a dose-response manner to determine an IC$_{50}$ value.

Compounds inhibiting PAF binding by less than 45% at a 50 mM concentration were considered inactive and no further testing was done.

IC$_{50}$ values were determined on active compounds in subsequent tests. Three or more compound doses must inhibit $^3$H-PAF binding between 15-85%. Using a computer program, % displacement data was transformed (logit) and a least squares linear regression was performed on the data meeting the 15-85% requirement to determine IC$_{50}$ values from data points derived from the same assay.

Inhibition of the Specific Binding of [$^3$H]PAF to Human Neutrophil Membranes: Human neutrophils were isolated from venous blood by dextran sedimentation followed by density gradient centrifugation using Ficoll-Hypaque [J. Biol. Chem., 254:7865-7869, 1979]. Residual red blood cells were removed by hypotonic lysis. Neutrophils were suspended in 50 mM Tris-HCl buffer, pH 7.7, and cells disrupted by sonication for 15 seconds on ice. Unbroken cells and nuclei were removed by slow speed centrifugation [1000xg, 10 min. 4°]. The resultant supernatant was centrifuged at 100,000xg for 60 minutes at 4°. The pellet was suspended in 10 mM Tris-HCl, pH 7.4, with 10 mM MgCl$_2$. Protein content was determined by the method of Lowry [J. Biol. Chem., 193:265-275, 1951]. Membranes were characterized for the concentration of binding sites [Bmax] and affinity for the ligand [Kd] using [3H]PAF by Scatchard analysis. Binding assays were conducted by incubating 50 mcg of membranes with 0.9 nM [3H]PAF and test compounds in 10 mM Tris-HCl buffer, pH 7.4, containing 0.1% bovine serum albumin. Nonspecific binding was determined by the addition of 1 μM PAF. Binding assay were done for 30 minutes at 24°. The assay was terminated by filtration through a Whatman GF/C glass filters and radioactivity determined by liquid scintillation counting.

Human Platelet Rich Plasma Aggregation Assay: Venous blood was collected from donors who fasted for 8 hours and were instructed not to use antiinflammatory drugs for 2 weeks prior to blood draw. Blood was collected into syringes containing 0.1 ml of 3.8% [w/v] citrate and centrifuged in polypropylene tubes at 150xg for 20 minutes at room temperature. The platelet rich plasma [PRP] was collected and let sit for 20 minutes at room temperature. Platelet activating factor [PAF] was diluted in 0.9% NaCI with 0 25% bovine serum albumin. Silicon treated cuvettes with stir bars were placed in the 37° heating block of the platelet aggregometer [Bio/Data Corporation, Platelet Aggregation Profiler, Model PAP-4]. PRP and test compound were added to cuvettes and aggregation monitored for 10-15 seconds at 37° with stirring. PAF was added and aggregation monitored for an additional 3 minutes. Peak aggregation was considered the peak of the first aggregation wave usually 45-60 seconds after PAF addition. Inhibition of aggregation was determined by the following: $1-[(\% \text{ aggregation in the presence of compound}) \div (\% \text{ maximal aggregation})]$. A log/logit transformation was used to determine half maximal inhibitory concentration of a test compound [$IC_{50}$].

| Compound | PAF induced platelet secretion ($IC_{50}$)M | PAF induced platelet aggregation ($IC_{50}$)M | Inhibition of $^3$H-PAF Binding to Human Platelet ($IC_{50}$)μM |
|---|---|---|---|
| 5-[4-(N-methyl-N-cyclohexylcarboxamido)benzyl]imidazo[4,5-c]pyridine | $7.2 \times 10^{-7}$ | $10^{-5}$ to $10^{-6}$ | 15.2 |
| 5-[4-(N-n-octylcarboxamido)benzyl]imidazo[4,5-c]pyridine | $10^{-6}$ to $10^{-7}$ | $10^{-5}$ to $10^{-6}$ | 11.0 |
| 5-[4-(N-n-decylcarboxamido)benzyl]imidazo[4,5-c]pyridine | $10^{-6}$ to $10^{-7}$ | $10^{-5}$ to $10^{-6}$ | 9.71 |
| 5-[4-(N-n-dodecylcarboxamido)benzyl]imidazo[4,5-c]pyridine | 1 to $5 \times$ to $10^{-7}$ | $10^{-6}$ to $10^{-7}$ | 11.9 |
| 5-[4-(N-2-decalyl-N-methylcarboxamido)benzyl]imidazo[4,5-c]pyridine | $10^{-6}$ | $10^{-5}$ to $10^6$ | 13.2 |
| 5-[4-(N-2-(2,4-4-trimethyl pentyl carboxamide)benzyl]imidazo[4,5-c]pyridine | $10^{-6}$ | $10^{-5}$ | 22.3 |
| 5-[4-(N,N-diisopropyl carboxamido)benzyl]imidazo[4,5-c]pyridine | $10^{-7}$ to $10^8$ | $10^{-5}$ to $10^{-6}$ | 7.65 |
| 5-[4-(N,N-dicyclopentyl carboxamido)benzyl]imidazo[4,5-c]pyridine | $10^{-8}$ to $10^{-9}$ | $10^{-7}$ to $5 \times 10^{-8}$ | 0.31 |
| 5-[4-(N-cyclohexylcarboxamido)benzyl]imidazo[4,5-c]pyridine | $10^{-6}$ to $10^{-7}$ | $10^{-5}$ | 19.3 |
| 5-[4-(N-ethyl-N-cyclohexyl carboxamido)carboxamido)benzyl]imidazo[4,5-c]pyridine | $10^{-7}$ to $10^{-6}$ | $10^{-6}$ to $10^{-5}$ | 5.20 |
| 5-[4-(N-isopropyl-N-cyclohexyl carboxamido)benzyl]imidazo[4,5-c]pyridine | $10^{-8}$ | $10^{-7}$ to $10^{-8}$ | 0.17 |
| 5-[4-(N-sec. butyl-N-cyclohexylcarboxamido)benzyl]imidazo[4,5-c]pyridine | $10^{-8}$ to $10^{-9}$ | $10^{-7}$ to $5 \times 10^{-8}$ | 0.58 |
| 5-[4-(N-isobutyl-N-cyclohexylcarboxamido)benzyl]imidazo[4,5-c]pyridine | $10^{-7}$ | $10^{-6}$ | 2.82 |
| 5-[4-(N-3-pentyl-N-cyclohexylcarboxamido)benzyl]imidazo[4,5-c]pyridine | $10^{-7}$ to $10^{-8}$ | $10^{-6}$ to $10^{-7}$ | — |
| 5-[4-(N-cyclopropyl-N-cyclohexylcarboxamido)benzyl]imidazo[4,5-c]pyridine | $10^{-6}$ to $10^{-7}$ | | 3.68 |
| 5-[4-(N-cyclobutyl-N-cyclohexylcarboxamido)benzyl]imidazo[4,5-c]pyridine | $10^{-8}$ to $10^{-9}$ | $10^{-7}$ to $10^{-8}$ | 0.0199 |
| 5-[4-(N-cyclopentyl-N-cyclohexylcarboxamido)benzyl]imidazo[4,5-c]pyridine | $10^{-8}$ to $10^{-9}$ | $10^{-7}$ to $10^{-8}$ | 0.32 |
| 5-(4-(N,N-dicyclohexyl carboxamidobenzyl)imidazo[4,5-c]pyridine | $10^{-8}$ | $10^{-6}$ to $10^{-7}$ | 1.06 |
| 5-[2-[4-(N-methyl-N-cyclohexylcarboxamido)phenyl]ethyl]imidazo[4,5-c]pyridine | $10^{-5}$ to $10^{-6}$ | $10^{-4}$ to $10^{-5}$ | — |
| 5-[3-[4-(N-methyl-N-cyclohexylcarboxamido)phenyl]propyl]imidazo[4,5-c]pyridine | $10^{-5}$ to $10^{-6}$ | $10^{-4}$ to $10^{-5}$ | 61.1 |
| 5-[4-(N,N-dicyclopentyl carboxamido)-2-methoxybenzyl]imidazo[4,5-c]pyridine | $10^{-8}$ to $10^{-9}$ | $10^{-7}$ to $10^{-8}$ | 0.055 |
| 5-[4-(N-cyclohexyl-N-cyclopentylcarboxamido)-2-methoxybenzyl]imidazo[4,5-c]pyridine | $10^{-8}$ to $10^{-9}$ | $10^{-8}$ | 0.0302 |
| 5-[4-(N-isopropyl-N-cyclohexylcarboxamido)2-methoxybenzyl]imidazo[4,5-c]pyridine | $10^{-8}$ | $10^{-7}$ to $10^{-8}$ | 0.0665 |
| 5-[4-(N-methyl-N-cyclohexyl | $10^{-6}$ to $10^{-7}$ | $10^{-5}$ to $10^{-6}$ | — |

-continued

| Compound | PAF induced platelet secretion (IC$_{50}$)$^M$ | Inhibition of $^3$H-PAF Binding to Human Platelet (IC$_{50}$)$^{\mu M}$ | Inhibition of Specific Binding of [$^3$H] PAF to Human Neutrophil Membranes (IC$_{50}$)$^{\mu M}$ | PAF induced Human Platelet Aggregation (IC$_{50}$)$^{\mu M}$ |
|---|---|---|---|---|
| carboxamido)-2-methoxybenzyl]imidazo[4,5-c]pyridine | | | | |
| 5-[4-(N-cyclopentyl-N-cyclohexylcarboxamido)-2-fluorobenzyl]imidazo[4,5-c]pyridine | $10^{-8}$ to $10^{-9}$ | $10^{-7}$ to $10^{-8}$ | | 0.0755 |
| 5-[4-(N-isopropyl-N-cyclohexylcarboxamido)-2-fluorobenzyl]imidazo[4,5-c]pyridine | $10^{-7}$ to $10^{-8}$ | $10^{-7}$ to $10^{-8}$ | | 0.442 |
| 5-[4-(N-methyl-N-cyclohexylcarboxamido)-2-fluorobenzyl]imidazo[4,5-c]pyridine | $10^{-6}$ to $10^{-7}$ | $10^{-5}$ to $10^{-6}$ | | — |
| 5-[4-(N-tert.butyl-N-cyclohexylcarboxamido)benzyl]imidazo[4,5-c]pyridine | $10^{-8}$ to $10^{-9}$ | $10^{-7}$ to $10^{-8}$ | | 87.7% inhib (50 μM) |
| 5-[4-(N-phenyl-N-cyclopentylcarboxamido)benzyl]imidazo[4,5-c]pyridine | $10^{-6}$ to $10^{-7}$ | $10^{-6}$ | | 2.35 |
| 5-[4-(N-3-methylcyclohexyl-N-cyclopentylcarboxamido)benzyl]imidazo[4,5-c]pyridine | $10^{-8}$ to $10^{-9}$ | $10^{-7}$ to $10^{-8}$ | | 0.074 |
| 5-[4-(N-4-methylcyclohexyl-N-cyclopentylcarboxamido)benzyl]imidazo[4,5-c]pyridine | $10^{-7}$ to $10^{-8}$ | $10^{-6}$ to $10^{-7}$ | | 0.75 |
| 5-[3-(N-methyl-N-cyclohexylcarboxamido)benzyl]imidazo[4,5-c]pyridine | $10^{-4}$ to $10^{-5}$ | $10^{-4}$ to $10^{-5}$ | | 38% inhib (50 μM) |
| 5-[3-(N-isopropyl-N-cyclohexylcarboxamido)benzyl]imidazo[4,5-c]pyridine | $10^{-5}$ to $10^{-6}$ | $10^{-4}$ to $5 \times 10^{-5}$ | | 26.1% inhib (50 μM) |
| 5-[4-(N,N-dicyclopentylcarboxamido)benzyl]-4-methylimidazo[4,5-c]pyridine | $10^{-7}$ to $10^{-8}$ | $10^{-7}$ to $10^{-8}$ | | 0.188 |
| 5-[4-(N,N-dicyclopentylcarboxamido)benzyl]-2-methylimidazo[4,5-c]pyridine | $10^{-6}$ to $10^{-7}$ | $10^{-5}$ to $10^{-6}$ | | 70.8% inhib (50 μM) |
| N-cyclopentyl-N-(3,5-dimethylcyclohexyl)-4-(5H-imidazo[4,5-c]pyridin-5-ylmethyl)-2-methoxybenzamide | $10^{-9}$ | | | 0.001 |
| N-cyclohexyl-N-cyclopentyl-4-(5H-imidazo[4,5-c]pyridin-5-ylmethyl)-3-methylbenzamide | $2 \times 10^{-9}$ | | | 0.018 |
| N-cyclopentyl-N-(3,5-dimethylcyclohexyl)-4-(5H-imidazo[4,5-c]pyridin-5-ylmethyl)-2-methoxybenzamide | $10^{-9}$ | 0.001 | | |
| N-cyclohexyl-N-cyclopentyl-4-(5H-imidazo[4,5-c]pyridin-5-ylmethyl)-3-methylbenzamide | $2 \times 10^{-9}$ | 0.018 | | |
| N-cyclohexyl-4-[[4-(1,1-dimethylethyl)-5H-imidazo[4,5-c]pyridin-5-yl-]methyl]-3-methoxy-N-(1-methyl-ethyl)-benzamide | | 37% (10 μM) | | |
| N-cyclopentyl-N-(3,5-dimethylcyclohexyl)-2-methoxy-4-[(7-methoxy-4-methyl-5H-imidazo-[4,5-c]pyridin-5-yl)methyl]benzamide | | 0.006 | .022 | .097 |
| N-cyclopentyl-N-(3,5-dimethylcyclohexyl)-2-methoxy-4- | | 0.009 | .019 | .033 |

-continued

| | | | |
|---|---|---|---|
| [(4-methyl-5H-imidazo[4,5-c]pyridin-5-yl)methyl]benzamide | | | |
| N-cyclohexyl-3-methoxy-N-(1-methylethyl)-4-[(4-methyl-5H-imidazo[4,5-c]pyridin-5-yl)methyl]benzamide | 0.065 | 0.35 | .007 |
| N-cyclobutyl-N-cyclohexyl-2-methoxy-4-[(4-methyl-5H-imidazo[4,5-c]pyridin-5-yl)methyl]benzamide | 0.003 | | |

What we claim is:

1. A compound of the formula

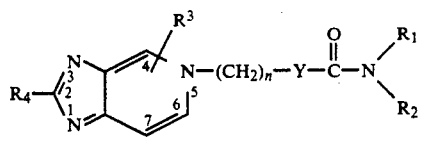

or a pharmaceutically acceptable acid addition salt thereof, wherein $R_1$ and $R_2$ are each independently selected from straight or branched chain alkyl of 1 to 15 carbon atoms; cycloalkyl having 3 to 8 carbon atoms; or substituted cycloalkyl which can be substituted one or more by alkyl of 1 to 6 carbon atoms;

Y is phenyl or phenyl substituted by alkoxy having 1 to 6 carbon atoms;

n is 1; $R_3$ is a group substituted at one or more of the 4, 6, or 7 position of the pyridine ring said group being independently selected from hydrogen, alkyl having 1 to 6 carbon atoms and alkoxy having 1 to 6 carbon atoms; and $R_4$ is hydrogen.

2. A compound according to claim 1 which is N-cyclohexyl-4-[[4-(1,1-dimethylethyl)-5H-imidazo[4,5-c]pyridin-5-yl]methyl]-3-methoxy-N-(1-methylethyl)-benzamide.

3. A compound according to claim 1 which is N-cyclopentyl-N-(3,5-dimethylcyclohexyl)-2-methoxy-4-[(7-methoxy-4-methyl-5H-imidazo [4,5-c]pyridin-5-yl]methyl)benzamide.

4. A compound according to claim 1 which is N-cyclopentyl-N-(3,5-dimethylcyclohexyl)-2-methoxy-4-[(4-methyl-5H-imidazo[4,5-c]pyridin-5-yl)methyl]benzamide.

5. A compound according to claim 1 which is N-cyclohexyl-3-methoxy-N-(1-methylethyl)-4-[(4-methyl-5H-imidazo[4,5-c]pyridin-5-yl)methyl]benzamide.

6. A compound according to claim 1 which is N-cyclobutyl-N-cyclohexyl-2-methoxy-4-[(4-methyl-H-imidazo[4,5-c]pyridin-5-yl)methyl]benzamide.

7. A pharmaceutical composition useful for treating diseases or disorders mediated by Platelet-activating Factor comprising an effective amount of at least one compound according to claim 1, together with one or more non-toxic pharmaceutically acceptable carriers.

8. A pharmaceutical composition according to claim 7 wherein said compound is selected from the group consisting of N-cyclohexyl-4-[[4-(1,1-dimethylethyl)-5H-imidazo[4,5-c]pyridin-5-yl]methyl]-3-methoxy-N-(1-methylethyl)benzamide;

N-cyclopentyl-N-(3,5-dimethylcyclohexyl)-2-methoxy-4-[(7-methoxy-4-methyl-5H-imidazo[4,5-c]pyridin-5-yl]methyl)benzamide;

N-cyclopentyl-N-(3,5-dimethylcyclohexyl)-2-methoxy-4-[(4-methyl-5H-imidazo[4,5-c]pyridin-5-yl)methyl]-benzamide; N-cyclohexyl-3-methoxy-N-(1-methylethyl)-4-[(4-methyl-5H-imidazo[4,5-c]pyridin-5-yl)methyl]benzamide; and N-cyclobutyl-N-cyclohexyl-2-methoxy-4-[(4-methyl-5H-imidazo[4,5-c]pyridin-5-yl)methyl]benzamide.

9. A method for treating diseases or disorders mediated by Platelet-activating Factor comprising administering a therapeutically effective dose of at least one compound of claim 1 to a mammal in need of such treatment.

10. A method according to claim 9 wherein said compound is selected from the group consisting of N-cyclohexyl-4-[[4-(1,1-dimethylethyl)-5H-imidazo[4,5-c]pyridin-5-yl]methyl]-3-methoxy-N-(1-methylethyl)-benzamide;

N-cyclopentyl-N-(3,5-dimethylcyclohexyl)-2-methoxy-4-[(7-methoxy-4-methyl-5H-imidazo[4,5-c]pyridin-5-yl]methyl)benzamide;

N-cyclopentyl-N-(3,5-dimethylcyclohexyl)-2-methoxy-4-[(4-methyl-5H-imidazo[4,5-c]pyridin-5-yl)methyl]-benzamide;

N-cyclohexyl-3-methoxy-N-(1-methylethyl)-4-[(4-methyl-5H-imidazo[4,5-c]pyridin-5-yl)methyl]benzamide; and N-cyclobutyl-N-cyclohexyl-2-methoxy-4-[(4-methyl-5H-imidazo[4,5-c]pyridin-5-yl)methyl]benzamide.

* * * * *

UNITED STATES PATENT AND TRADEMARK OFFICE
CERTIFICATE OF CORRECTION

PATENT NO. : 5,302,601
DATED : April 12, 1994
INVENTOR(S) : Khannal, et al.

It is certified that error appears in the above-indentified patent and that said Letters Patent is hereby corrected as shown below:

Column 2, line 34, reading "having 1 to" should read -- having 1 to 6 --.

Column 5, line 17, reading "carbon atoms:" should read -- carbon atoms; --.

Column 10, line 64, reading "intermediate S." should read -- intermediate 8. --.

Column 14, line 5, reading "Of 13" should read -- of 13 --.

Column 14, line 6, reading "pd/C" should read -- Pd/C --.

Column 15, line 24, reading "POCl$_3$at" should read -- POCl$_3$ at --.

Column 16, line 55, that part of the formula reading

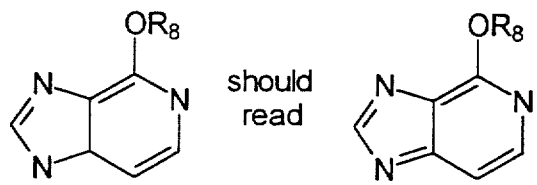

Column 17, line 61, reading "(XvIII)." should read -- (XVIII). --.

UNITED STATES PATENT AND TRADEMARK OFFICE
CERTIFICATE OF CORRECTION

PATENT NO. : 5,302,601
DATED : April 12, 1994
INVENTOR(S) : Khannal, et al.

It is certified that error appears in the above-indentified patent and that said Letters Patent is hereby corrected as shown below:

Column 19, line 49, reading "IN HCl," should read -- 1N HCl, --.

Column 22, line 27, reading "change" should read -- range --.

Column 22, line 30, reading "cyclpentanone" should read -- cyclopentanone --.

Column 24, line 13, reading "(22. Z is OMe) should read -- (22, Z is OMe) --.

Column 27, line 45, reading "imidazo 4.5-c]" should read -- imidazo[4,5-c] --.

Column 28, line 24, reading "N, 15 78 m.p." should read -- N, 15.78 m.p. --.

Column 37, line 4, reading "cyclopentyl-3,5" should read -- cyclopentyl, N-3,5 --.

Column 42, line 46, reading "5-4{-" should read -- 5-[4{- --.

Column 46, line 41, reading "57-50°" should read -- 57-59° --.

At column 47, lines 1, 30 and 67 (twice), all occurrences reading "(1h, s)" should read -- (1H, s) --.

At column 47, lines 2, 30, 31, 65, 66 and 67, all occurrences reading "(1h, d," should read -- (1H, d, --.

UNITED STATES PATENT AND TRADEMARK OFFICE
CERTIFICATE OF CORRECTION

PATENT NO. : 5,302,601          Page 3 of 5

DATED : April 12, 1994

INVENTOR(S) : Khannal, et al.

It is certified that error appears in the above-indentified patent and that said Letters Patent is hereby corrected as shown below:

Column 47, line 35, reading "imidazo 4,5" should read -- imidazo]4,5 --.

Column 47, line 57, reading "($Na_2SO_4$)" should read -- ($Na_2SO_4$) --.

Column 47, line 65, reading "(1h, s," should read -- (1H, s, --.

Column 47, line 66, reading "(1h, d)" should read -- (1H, d) --.

At column 48, line 22, column 50, line 55, column 51, lines 7 and 25, column 56, lines 7, 23 and 56, all occurrences reading "-1h-" should read -- -1H- --.

Column 48, line 57, reading "2 Hz, 1h)" should read -- 2 Hz, 1H) --.

Column 49, line 21, reading "17 7 g," should read -- 17.7 g, --.

Column 49, line 40, reading "7.5 Hz, 2H)," should read -- 7.5 Hz, 2H), 7.23 (t, J = 7.5 Hz, 1H), 7.13 (d, J = 7.5 Hz, 2H), --.

At column 49, lines 40 and 41, both instances reading "(broad s, 1h)" should read -- (broad s, 1H) --.

Column 49, line 49, reading "6 Hz, 1h)" should read -- 6 Hz, 1H) --.

Column 50, line 11, reading "(I00 ml," should read -- (100 ml, --.

UNITED STATES PATENT AND TRADEMARK OFFICE
CERTIFICATE OF CORRECTION

PATENT NO. : 5,302,601
DATED : April 12, 1994
INVENTOR(S) : Khannal, et al.

It is certified that error appears in the above-indentified patent and that said Letters Patent is hereby corrected as shown below:

Column 50, line 23, reading "O$_4$Si]" should read -- O$_4$Si· --.

Column 50, line 36, reading "Was" should read -- was --.

Column 51, line 2, reading "(s, 1h)" should read -- (S, 1H) --.

Column 51, line 22, reading "(s, 1h), 8.0 (s, 1h)" should read -- (s, 1H) 8.0 (s, 1H) --.

Column 51, line 34, reading "(s, 1h)" should read -- (s, 1H) --.

Column 51, line 54, reading "J Hz, 1h)" should read -- J Hz, 1H) --.

Column 52, line 5, reading "(s, 1h)" should read -- (s, 1H) --.

Column 52, line 6, reading "Hz, 1h)" should read -- Hz, 1H) --.

Column 52, line 22, reading "Hz, 1h); 7.I3" should read -- (Hz, 1H); 7.13 --.

Column 52, line 52, reading "2 HZ," should read -- 2 Hz, --.

Column 52, line 53, reading "(s, 1h)" should read -- (s, 1H) --.

Column 53, line 4, reading "(m, 1h)" should read -- (m, 1H) --.

Column 53, line 6, reading "8 Hz, 1h)" should read -- 8 Hz, 1H) --.

UNITED STATES PATENT AND TRADEMARK OFFICE
CERTIFICATE OF CORRECTION

PATENT NO. : 5,302,601
DATED : April 12, 1994
INVENTOR(S) : Khannal, et al.

It is certified that error appears in the above-indentified patent and that said Letters Patent is hereby corrected as shown below:

Column 53, line 28, reading "(m, 1h)" should read -- (m, 1H) --.

Column 54, line 47, reading "44(I)" should read -- 44(1) --.

At column 55, lines 34 and 35, both occurrences reading "10 Hz, 1h)" should read -- 10 Hz, 1H).

Column 57, line 8, reading "4-[4-" should read -- 4-[[4- --.

Column 57, line 9, reading "methyl1" should read -- methyl] --.

Column 57, line 32, reading "1h), 8.0 (s, 1h)" should read -- 1H), 8.0 (s, 1H) --.

Column 57, line 43, reading "(CAMP)" should read -- (cAMP) --.

Column 58, line 53, reading "The Assay Methods: compounds" should read -- The compounds --.

Column 59, line 22, reading "14 ml Was" should read -- 14 ml was --.

Column 60, line 27, reading "Tris-HCI" should read -- Tris-HCl --.

Signed and Sealed this

Nineteenth Day of December, 1995

BRUCE LEHMAN

*Attesting Officer*   *Commissioner of Patents and Trademarks*